(12) United States Patent
Jiao et al.

(10) Patent No.: US 7,473,703 B2
(45) Date of Patent: Jan. 6, 2009

(54) HETEROCYCLIC ARYLSULFONAMIDOBENZYLIC COMPOUNDS

(75) Inventors: Xian Yun Jiao, San Mateo, CA (US); Frank Kayser, San Francisco, CA (US); David J. Kopecky, San Francisco, CA (US); Sharon McKendry, Redwood Shores, CA (US); Derek E. Piper, Foster City, CA (US); Andrew K. Shiau, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 24 days.

(21) Appl. No.: 11/501,594

(22) Filed: Aug. 8, 2006

(65) Prior Publication Data
US 2006/0270718 A1  Nov. 30, 2006

Related U.S. Application Data

(63) Continuation of application No. 10/354,923, filed on Jan. 29, 2003, now Pat. No. 7,112,606.

(60) Provisional application No. 60/353,496, filed on Jan. 30, 2002.

(51) Int. Cl.
*A61K 31/40* (2006.01)
*C07D 207/325* (2006.01)

(52) U.S. Cl. .................. 514/427; 548/562
(58) Field of Classification Search ............. 514/427; 548/562
See application file for complete search history.

(56) References Cited

U.S. PATENT DOCUMENTS

| | | | |
|---|---|---|---|
| 3,281,466 A | 10/1966 | Stacker et al. | |
| 3,405,177 A | 10/1968 | Jones et al. | |
| 4,093,738 A | 6/1978 | Hubele | |
| 4,093,742 A | 6/1978 | Neustadt | |
| 4,107,303 A | 8/1978 | Aldrich et al. | |
| 4,166,123 A | 8/1979 | Harrison et al. | |
| 4,187,232 A | 2/1980 | Evans et al. | |
| 4,199,597 A | 4/1980 | Neustadt et al. | |
| 4,204,002 A | 5/1980 | Hubele | |
| 4,218,448 A | 8/1980 | Aldrich et al. | |
| 4,230,635 A | 10/1980 | Neustadt | |
| 4,235,928 A | 11/1980 | Eicken et al. | |
| 4,240,979 A | 12/1980 | Baumann et al. | |
| 4,251,534 A | 2/1981 | Aldrich et al. | |
| 4,251,659 A | 2/1981 | Aldrich et al. | |
| 4,267,193 A | 5/1981 | Neusladt et al. | |
| 4,501,746 A | 2/1985 | Krumkains | |
| 5,310,760 A | 5/1994 | Washburn et al. | |
| 5,439,915 A | 8/1995 | Commons et al. | |
| 5,861,532 A | 1/1999 | Nuss et al. | |
| 5,883,106 A | 3/1999 | Stevens et al. | |
| 5,952,368 A | 9/1999 | Kertesz et al. | |
| 6,030,991 A | 2/2000 | Chan et al. | |
| 6,090,853 A | 7/2000 | Wetterich et al. | |
| 6,156,766 A | 12/2000 | Arita et al. | |
| 6,162,830 A | 12/2000 | Connor et al. | |
| 6,174,905 B1 | 1/2001 | Suzuki et al. | |
| 6,191,170 B1 | 2/2001 | Medina | |
| 6,197,798 B1 | 3/2001 | Fink et al. | |
| 6,201,013 B1 | 3/2001 | Blown et al. | |
| 6,211,241 B1 | 4/2001 | Islam et al. | |
| 6,211,242 B1 | 4/2001 | Setoff et al. | |
| 6,214,880 B1 | 4/2001 | Houze | |
| 6,242,493 B1 | 6/2001 | Gareau et al. | |
| 6,316,503 B1 | 11/2001 | U et al. | |
| 7,071,358 B2 * | 7/2006 | Jiao et al. ............ 564/92 |
| 2003/0220339 A1 | 11/2003 | Jiao et al. | |

FOREIGN PATENT DOCUMENTS

| | | |
|---|---|---|
| BE | 872311 | 5/1979 |
| DE | 25 15113 | 10/1975 |
| DE | 26 25 242 | 12/1976 |
| DE | 2625 227 | 12/1976 |
| DE | 44 37 999 | 5/1996 |
| DE | 44 38 020 | 5/1996 |
| EP | 0 012 428 | 6/1980 |
| EP | 0 013 360 | 7/1980 |
| EP | 0 019 745 | 12/1980 |
| EP | 0 023 669 | 2/1981 |
| EP | 0193 249 | 9/1986 |
| EP | 0 919 542 | 6/1999 |
| GB | 1 507 340 | 4/1978 |
| JP | 6323822 | 2/1986 |
| JP | 0756392 | 7/1995 |
| JP | 07118215 | 7/1995 |
| WO | WO94/21611 | 9/1994 |
| WO | WO97/31637 | 9/1997 |
| WO | WO9735838 | 10/1997 |

(Continued)

OTHER PUBLICATIONS

Gong et al. (Expert Opin. Ther. Targets 2004 8(1), 49-54).*
Geyeregger et al. (Cell. Mol. Life Sci. 2006, 63, 524-539).*
Bennett et al. (Expert Opin. Ther. Patents 2006, 16(12), 1673-1699).*
Abramovitch, R., et al., "Mechanism of direct side-chain acylamination and aminoarylation of 2- and 4- picoline l-oxides" J. Chem Soc. 11:561-2, Database CAS Online, Chem Abstr., Accession No. 1981:568016 1981.
Beckwith, A., et al., "Tandem radical translocation and homolytic aromatic substitution: a convenient and efficient route to oxindoles" J. Chem. Soc. Chem. Commun. pp. 977-978 (1995).

(Continued)

*Primary Examiner*—Kamal A Saeed
*Assistant Examiner*—Jason Nolan
(74) *Attorney, Agent, or Firm*—Jones Day

(57) ABSTRACT

Heterocyclic arylsulfonamidobenzylic compounds are provided which are useful in treating lipid disorders, metabolic disorders and cell-proliferative diseases.

9 Claims, No Drawings

FOREIGN PATENT DOCUMENTS

| WO | WO99/06382 | 2/1999 |
| --- | --- | --- |
| WO | WO99/40064 | 8/1999 |
| WO | WO99/44987 | 9/1999 |
| WO | WO00/26186 | 5/2000 |
| WO | WO00/46203 | 8/2000 |
| WO | WO00/54759 | 9/2000 |
| WO | WO01/60818 | 8/2001 |

OTHER PUBLICATIONS

Cao et al., 2003 "Antidiabetic Action of a Liver X Receptor Agonist Mediated by Inhibition of Hepatic Gluconeogenesis," The Journal of Biological Chemistry, 278(2):1131-1136.

Chisholm et al., Journal of Lipid Research, vol. 44, 2003, pp. 2039-2048.

Database CAS Online on STN, Chem. Abstr., Accession No. 1998:1455, WO 9746524 Al (F. Hoffman- La Roche A.G., Switz.) Dec. 11, 1997, abstract.

Grefhorst et al Am J Physicl Endocrinol Metab. Jun. 7, 2005: [Epub ahead of print], Differential effects of pharmacological liver X receptor activation on hepatic and peripheral insulin sensitivity in lean and ob/ob mice.

Joseph et al., 2003 "Synthetic LXR Ligand Inhibits the Development of Atherosclerosis in Mice," PNAS, 99(11):7604-7609.

Laffitte et al., 2002 "Orphan Nuclear Receptors Find a Home in the Arterial Wall," Current Atherosclerosis Reports, 4(3):213-221.

Le Blanc, S., et al., "New access to spiranc β-lactams" Tetrahedron Lett 33(15):1993.1996 (1992).

Lund et al., Artedoscler Thromb Vasc Biol., Jul. 2003, 1169-1177.

Masazlimi I. et al., "Photochemical synthesis of spiro-β-lactams" J. Chem. Soc. Chem. Commun. pp. 758-759 (1984).

Masazlimi, I., et al., "Photochemistry of 2-(N-aryl-N-alkylamino) cydohex-2-enones: formation of spiro-β-ladams" Chem. Pharm. Bull. 34(12):4997-5004 (1986).

Miryan et al., "Derivatives of pyridinecarboxylic adds. Synthesis and antiexudadve effect of fluorinated derivatives of nicolinamide and isonicolinamide" Database Chemabs 'Online! Chemical Abstract Service, accession No. 86:139798, 11(1):70-2 1997 [Russian Abstract].

Polishchlick, V. et al., "Electron paramagnetic resonance spectra of 2-arylpolyfluoroisopropyl radicals" Database Chemabs 'Online! Chemical Abstract Service accession No. 91:4737, 3:659.661 (1979) [Russian Abstract].

Schwarz. M., et al., "Solid-phase synthesis of 3,5-disubstituted 2,3-dihydro-1,5-benzothiazepin-r(5H)- ones" J. Org. Chem. 64:2219-2231 (1999).

Stein et al., Biochimica et Biophysica Acta 1686 (2004), 24-29.

Chkanikov, N. et al., "Hexafluoroacetone and methyl trifluoropyruvate as precursors of modified esters of n-aryl-n-phenyl-a-amino adds" Bulletin of the Russian Academy of Sciences 41(8) Part 2:1415-1424 (1993).

CAS Registry No. CA62:16091f, Gilbert et al., "Perhalo ketones-(VI) aromatic amino derivs. of the penhaloaoetones", Jan. 24, 1992.

* cited by examiner

HETEROCYCLIC ARYLSULFONAMIDOBENZYLIC COMPOUNDS

CROSS-REFERENCES TO RELATED APPLICATIONS

This application is a continuation of U.S. patent application Ser. No. 10/354,923, filed Jan. 29, 2003, now U.S. Pat. No. 7,112,606, which claims the benefit of Provisional Application No. 60/353,496, filed Jan. 30, 2002, and is related in subject matter to U.S. application Ser. No. 10/354,922, filed Jan. 29, 2003, now U.S. Pat. No. 7,071,358, the disclosures of which are incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). Excess accumulation of cholesterol in the arterial walls can result in atherosclerosis, which is characterized by plaque formation. The plaques inhibit blood flow, promote clot formation and can ultimately cause heart attacks, stroke and claudication. Development of therapeutic agents for the treatment of atherosclerosis and other diseases associated with cholesterol metabolism has been focused on achieving a more complete understanding of the biochemical pathways involved. Most recently, liver X receptors (LXRs) were identified as key components in cholesterol homeostasis.

The LXRs were first identified as orphan members of the nuclear receptor superfamily whose ligands and functions were unknown. Two LXR proteins (α and β) are known to exist in mammals. The expression of LXRα is restricted, with the highest levels being found in the liver, and lower levels found in kidney, intestine, spleen, and adrenals (see Willy, et al., *Genes Dev.* 9(9):1033-45 (1995)). LXRfβ is rather ubiquitous, being found in nearly all tissues examined. Recent studies on the LXRs indicate that they are activated by certain naturally occurring, oxidized derivatives of cholesterol, including 22(R)-hydroxycholesterol, 24(S)-hydroxycholesterol and 24,25(S)-epoxycholesterol (see Lehmann, et al., *J Biol. Chem.* 272(6):3137-3140 (1997)). The expression pattern of LXRs and their oxysterol ligands provided the first hint that these receptors may play a role in cholesterol metabolism (see Janowski, etal., *Nature* 383:728-731 (1996)).

As noted above, cholesterol metabolism in mammals occurs via conversion into steroid hormones or bile acids. The role of LXRs in cholesterol homeostasis was first postulated to involve the pathway of bile acid synthesis, in which cholesterol 7α-hydroxylase (CYP7A) operates in a rate-limiting manner. Support for this proposal was provided when additional experiments found that the CYP7A promoter contained a functional LXR response element that could be activated by RXR/LXR heterodimers in an oxysterol- and retinoid-dependent manner. Confirmation of LXR function as a transcriptional control point in cholesterol metabolism was made using knockout mice, particularly those lacking the oxysterol receptor LXRα (see Peet, et al., *Cell* 93:693-704 (1998)).

Mice lacking the receptor LXRα (e.g., knockout or (−/−) mice) lost their ability to respond normally to increases in dietary cholesterol and were unable to tolerate any cholesterol in excess of that synthesized de novo. LXRα (−/−) mice did not induce transcription of the gene encoding CYP7A when fed diets containing additional cholesterol. This resulted in an accumulation of large amounts of cholesterol and impaired hepatic function in the livers of LXRα (−/−) mice. These results further established the role of LXRα as the essential regulatory component of cholesterol homeostasis. LXRα is also believed to be involved in fatty acid synthesis. Accordingly, regulation of LXRα (e.g., use of LXRα agonist or antagonists) could provide treatment for a variety of lipid disorders including obesity and diabetes.

In view of the importance of LXRs, and particularly LXRαs to the delicate balance of cholesterol metabolism and fatty acid biosynthesis, we describe modulators of LXRs which are useful as therapeutic agents or diagnostic agents for the treatment of disorders associated with bile acid and cholesterol metabolism, including cholesterol gallstones, atherosclerosis, lipid storage diseases, obesity, and diabetes. The agents described herein are also useful for disease states associated with serum hypercholesterolemia, such as coronary heart disease.

BRIEF SUMMARY OF THE INVENTION

In one aspect, the present invention provides compounds having the formula:

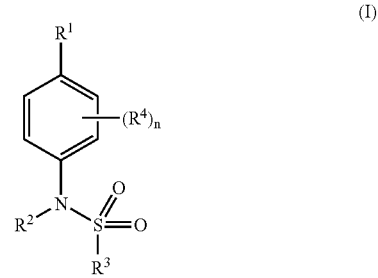

(I)

wherein $R^1$ is selected from:

(Ia)

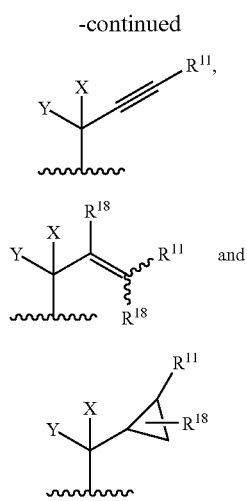

wherein $R^{11}$ is heteroaryl, optionally substituted with from one to five substituents independently selected from halogen, cyano, nitro, $R^{14}$, $OR^{13}$, $SR^{13}$, $N(R^{13})_2$, $NHSO_2R^{14}$, $NHC(O)R^{13}$, phenyl, phenyl($C_1$-$C_8$)alkyl, and phenyl($C_2$-$C_8$)heteroalkyl; wherein each $R^{13}$ is independently selected from H, ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl and each $R^{14}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl.

Each $R^{18}$ is independently selected from H, ($C_1$-$C_8$)alkyl, ($C_2$-$C_8$)heteroalkyl, halo($C_1$-$C_8$)alkyl, aryl and heteroaryl.

In each of the $R^1$ groups above, the component X represents H, $NH_2$, $NHR^{15}$, $NHSO_2R^{15}$, OH or $OR^{15}$, wherein $R^{15}$ is ($C_1$-$C_8$)alkyl, ($C_3$-$C_8$)alkenyl, ($C_3$-$C_8$)alkynyl, ($C_2$-$C_8$)heteroalkyl or halo($C_1$-$C_8$)alkyl; and the component Y is H, ($C_1$-$C_8$)alkyl, ($C_3$-$C_8$)cycloalkyl, ($C_3$-$C_8$)alkenyl, ($C_3$-$C_8$)alkynyl or ($C_2$-$C_8$)heteroalkyl; with the proviso that when Y is a substituted ($C_1$-$C_8$)alkyl, the substituents are other than fluorine atoms.

Returning to formula I, $R^2$ is selected from H, ($C_1$-$C_8$)alkyl, ($C_2$-$C_8$)heteroalkyl, ($C_3$-$C_8$)alkenyl, ($C_3$-$C_8$)alkynyl, ($C_3$-$C_8$)cycloalkyl and ($C_4$-$C_8$)cycloalkyl-alkyl, wherein any alkyl portions of $R^2$ are optionally substituted with from one to three substituents independently selected from halogen, nitro, cyano, hydroxy, oxo and amino; and $R^3$ is selected from aryl and heteroaryl, the aryl or heteroaryl group being optionally substituted with from one to five substituents independently selected from halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl, or two $R^{16}$ groups attached to the same nitrogen atom are combined to form a five- to eight-membered ring. Optionally, $R^2$ and $R^4$ are combined to form a five- to six-membered fused ring containing from 1 to 3 heteroatoms selected from N, O and S.

The subscript n is an integer of from 0 to 3, indicating the presence or absence of substituents on the phenyl ring core of formula I. Each of the $R^4$ substituents is independently selected from halogen, cyano, nitro, $R^{17}$, $OR^{17}$, $SR^{17}$, $COR^{17}$, $CO_2R^{17}$, $N(R^{17})_2$ and $CON(R^{17})_2$, wherein each $R^{17}$ is independently selected from H, ($C_1$-$C_8$)alkyl, ($C_3$-$C_8$)alkenyl, ($C_3$-$C_8$)alkynyl, ($C_2$-$C_8$)heteroalkyl or halo($C_1$-$C_8$)alkyl, or two $R^{17}$ groups attached to the same nitrogen atom are combined to form a five- to eight-membered ring.

In addition to the compounds provided in formula I, pharmaceutically acceptable salts thereof are also provided.

In yet another aspect, the present invention provides methods for modulating LXR in a cell by administering to or contacting the cell with a composition containing a compound of Formula I above.

In still another aspect, the present invention provides methods for treating LXR-responsive diseases by administering to a subject in need of such treatment a composition containing a compound of Formula I. These methods are particularly useful for the treatment of pathology such as obesity, diabetes, hypercholesterolemia, atherosclerosis, and hyperlipoproteinemia. In certain embodiments, the compound can be administered to the subject in combination with an additional anti-hypercholesterolemic agent, for example, bile acid sequestrants, nicotinic acid, fibric acid derivatives or HMG CoA reductase inhibitors.

The present compounds can exert their effects either systemically (the compounds permeate the relevant tissues, such as liver, upon entrance into the bloodstream) or locally (for example, by modulating LXR function of intestinal epithelial cells following oral administration, without necessitating the compounds' entrance into the bloodstream). In some disease states, some preferred compounds will be those with good systemic distribution, while, in other instances, preferred compounds will be those that can work locally on the intestinal track or on the skin without penetrating the bloodstream.

Certain compounds of the present invention are antiproliferative and can be used in compositions for treating diseases associated with abnormal cell proliferation (e.g., cancer). Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

BRIEF DESCRIPTION OF THE DRAWINGS

Not applicable.

DETAILED DESCRIPTION OF THE INVENTION

Definitions

As used herein, the term "heteroatom" is meant to include oxygen (O), nitrogen (N), sulfur (S) and silicon (Si).

The term "alkyl," by itself or as part of another substituent, means, unless otherwise stated, a straight or branched chain, or cyclic hydrocarbon radical, or combination thereof, which is fully saturated, having the number of carbon atoms designated (i.e. $C_1$-$C_8$ means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., $C_3$-$C_8$ means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo($C_1$-$C_4$)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo($C_1$-$C_4$)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term "heteroaryl" refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R"', —OC(O)R', —C(O)R', —CO$_2$R', —CONR'R", —OC(O)NR'R", —NR"C(O)R', —NR'—C(O)NR"R"', —NR'—SO$_2$NR"R"', —NR"CO$_2$R', —NH—C(NH$_2$)=NH, —NR'C(NH$_2$)=NH, —NH—C(NH$_2$)=NR', —S(O)R', —SO$_2$R', —SO$_2$NR"R", —NR"SO$_2$R, —CN and —NO$_2$, in a number ranging from zero to three, with those groups having zero, one or two substituents being particularly preferred. R', R" and R"' each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R"', —OC(O)R', —C(O)R', —CO$_2$R', —CONR'R", —OC(O)NR'R", —NR"C(O)R', —NR"CO$_2$R', —NR'—SO$_2$NR"R"', —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R"', —SO$_2$R', —SO$_2$NR'R", —NR"SO$_2$R, —CN and —NO$_2$.

Similarly, substituents for the aryl and heteroaryl groups are varied and selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R"', —NR'—SO$_2$NR"R"', —NH—C(NH$_2$)=NH, —NR'C(NH$_2$)=NH, —NH—C(NH$_2$)=NR', —S(O)R', —SO$_2$R', —SO$_2$NR'R", —NR"SO$_2$R, —N$_3$, —CH(Ph)$_2$, perfluoro(C$_1$-C$_4$)alkoxy and perfluoro(C$_1$-C$_4$)alkyl, in a number ranging from zero to the total number of open valences on the aromatic ring system; and where R', R" and R"' are independently selected from hydrogen, (C$_1$-C$_8$)alkyl and heteroalkyl, unsubstituted aryl and heteroaryl, (unsubstituted aryl)-(C$_1$-C$_4$)alkyl and (unsubstituted aryl)oxy-(C$_1$-C$_4$)alkyl. When the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as derined herein for "cycloalkyl". Typically, an aryl or heteroaryl group will have from zero to three substituents, with those groups having two or fewer substituents being preferred in the present invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO$_2$, —CO$_2$R', —CONR'R", —C(O)R', —OC(O)NR'R", —NR"C(O)R', —S(O)R', —SO$_2$R', —SO$_2$NR'R", —NR"SO$_2$R, —N$_3$, —CH(Ph)$_2$, perfluoro(C$_1$-C$_4$)alkoxy and perfluoro(C$_1$-C$_4$)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C$_1$-C$_4$)alkoxy and perfluoro(C$_1$-C$_4$)alkyl.

It is to be understood that the substituent —CO$_2$H, as used herein, includes bioisosteric replacements therefor, such as:

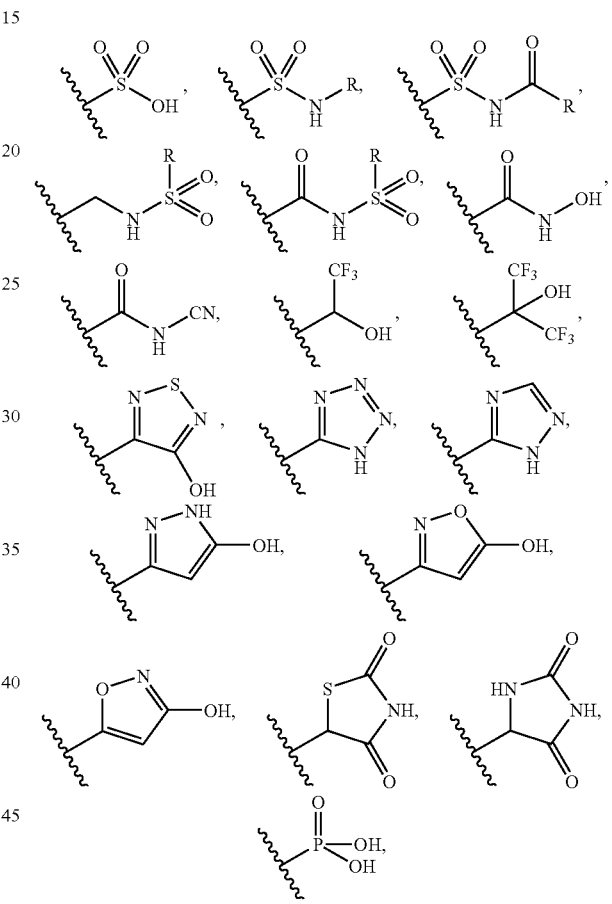

and the like. See, e.g., *The Practice of Medicinal Chemistry*; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) *J. Pharm. Sci.* 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The terms "modulate", "modulation" and the like refer to the ability of a compound to increase or decrease the function and/or expression of LXR, where LXR function may include transcription regulatory activity and/or protein-binding. Modulation may occur in vitro or in vivo. Modulation, as described herein, includes antagonism, agonism, partial antagonism and/or partial agonism of a function or characteristic associated with LXR, either directly or indirectly, and/or the upregulation or downregulation of LXR expression, either directly or indirectly. Agonists are compounds that, e.g., bind to, stimulate, increase, open, activate, facilitate, enhance activation, activate, sensitize or upregulate signal transduction. Antagonists are compounds that, e.g., bind to, partially or totally block stimulation, decrease, prevent, inhibit, delay activation, inactivate, desensitize, or downregulate signal transduction. A modulator preferably inhibits LXR function and/or downregulates LXR expression. More preferably, a modulator inhibits or activates LXR function and/or downregulates or upregulates LXR expression. Most preferably, a modulator activates LXR function and/or upregulates LXR expression. The ability of a compound to modulate LXR function can be demonstrated in a binding assay or a cell-based assay, e.g., a transient transfection assay.

As used herein, "diabetes" refers to type I diabetes mellitus juvenile onset diabetes, insulin dependent-diabetes mellitus or IDDM) or type II diabetes mellitus (non-insulin-dependent diabetes mellitus or NIDDM), preferably, NIDDM.

As used herein, the term "LXR-mediated condition or disorder" refers to a condition or disorder characterized by inappropriate, e.g., less than or greater than normal, LXR activity. Inappropriate LXR functional activity might arise as the result of LXR expression in cells which normally do not express LXR, decreased LXR expression (leading to, e.g., lipid and metabolic disorders and diseases) or increased LXR expression. An LXR-mediated condition or disease may be completely or partially mediated by inappropriate LXR functional activity. However, an LXR-mediated condition or disease is one in which modulation of LXR results in some effect on the underlying condition or disorder (e.g., an LXR agonist results in some improvement in patient well-being in at least some patients).

As used herein, the term "LXR-responsive condition" or "LXR-responsive disorder" refers to a condition or disorder that responds favorably to modulation of LXR activity. Favorable responses to LXR modulation include alleviation or abrogation of the disease and/or its attendant symptoms, inhibition of the disease, i.e., arrest or reduction of the development of the disease, or its clinical symptoms, and regression of the disease or its clinical symptoms. An LXR-responsive condition or disease may be completely or partially responsive to LXR modulation. An LXR-responsive condition or disorder may be associated with inappropriate, e.g., less than or greater than normal, LXR activity. Inappropriate LXR functional activity might arise as the result of LXR expression in cells which normally do not express LXR, decreased LXR expression (leading to, e.g., lipid and metabolic disorders and diseases) or increased LXR expression. An LXR-responsive condition or disease may include an LXR-mediated condition or disease.

The term "therapeutically effective amount" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

General

The present invention provides compositions, compounds and methods for modulating LXR function in a cell. The compositions which are useful for this modulation will typically be those which contain an effective amount of an LXR-modulating compound.

In general, an effective amount of an LXR-modulating compound is a concentration of the compound that will produce at 50 percent increase/decrease in LXR activity in a cell-based reporter gene assay, or a biochemical peptide-sensor assay such as the assays described in co-pending applications Ser. No. 08/975,614 (filed Nov. 21, 1997) and Ser. No. 09/163,713 (filed Sep. 30, 1998).

EMBODIMENTS OF THE INVENTION

Compounds

In one aspect, the present invention provides compounds having the formula:

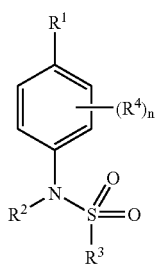

wherein $R^1$ is selected from

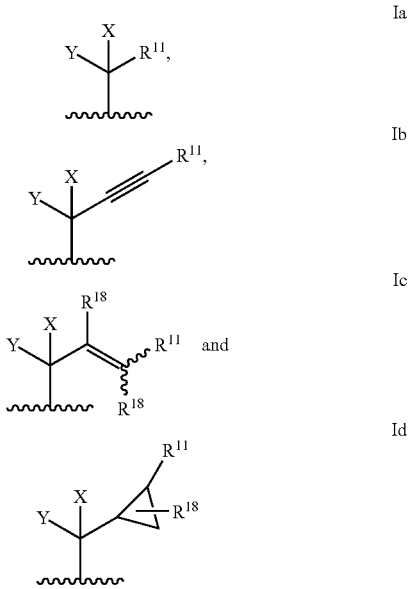

wherein $R^{11}$ is heteroaryl, preferably selected from the group consisting of pyrrolyl, imidazolyl, thiazolyl, oxazolyl, isoxazolyl, triazolyl, pyrazolyl, benzimidazolyl, benzthiazolyl, indolyl, thienyl, furyl, pyridyl, quinolinyl, isoquinolinyl, quinoxalinyl, pyrimidinyl, pyrazinyl and pyridazinyl. More preferably, $R^{11}$ is selected from the group consisting of pyrrolyl, imidazolyl, thiazolyl, oxazolyl, isoxazolyl, triazolyl and pyrazolyl, most preferably, pyrrolyl. Each of the recited heteroaryl groups is optionally substituted with from one to five substituents independently selected from the group consisting of halogen, cyano, nitro, $R^{14}$, $OR^{13}$, $SR^{13}$, $N(R^{13})_2$, $NHSO_2R^{14}$, $NHC(O)R^{13}$, phenyl, phenyl($C_1$-$C_8$)alkyl, and phenyl($C_2$-$C_8$)heteroalkyl; wherein each $R^{13}$ is independently selected from H, ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl and each $R^{14}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl; each $R^{18}$ is independently selected from the group consisting of H, ($C_1$-$C_8$)alkyl, ($C_2$-$C_8$)heteroalkyl, halo($C_1$-$C_8$)alkyl, aryl and heteroaryl; X is a member selected from the group consisting of H, $NH_2$, $NHR^{15}$, $NHSO_2R^{15}$, OH and $OR^{15}$, wherein $R^{15}$ is ($C_1$-$C_8$)alkyl, ($C_3$-$C_8$)alkenyl, ($C_3$-$C_8$)alkynyl, ($C_2$-$C_8$)heteroalkyl or halo($C_1$-$C_8$)alkyl; and Y is H, ($C_1$-$C_8$)alkyl, ($C_3$-$C_8$)cycloalkyl, ($C_3$-$C_8$)alkenyl, ($C_3$-$C_8$)alkynyl or ($C_2$-$C_8$)heteroalkyl; with the proviso that when Y is a substituted ($C_1$-$C_8$)alkyl, the substituents are other than fluorine atoms.

$R^2$ is selected from H, ($C_1$-$C_8$)alkyl, ($C_2$-$C_8$)heteroalkyl, ($C_3$-$C_8$)alkenyl, ($C_3$-$C_8$)alkynyl, ($C_3$-$C_8$)cycloalkyl and ($C_4$-$C_8$)cycloalkyl-alkyl, wherein any alkyl portions of $R^2$ are optionally substituted with from one to three substituents independently selected from halogen, nitro, cyano, hydroxy, oxo and amino, or optionally $R^2$ is combined with $R^4$ to form a five- to six-membered fused ring containing from 1 to 3 heteroatoms selected from N, O and S.

$R^3$ is selected from aryl and heteroaryl, the aryl or heteroaryl group being optionally substituted with from one to five substituents independently selected from the group consisting of halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl, or two $R^{16}$ groups attached to the same nitrogen atom are combined to form a five- to eight-membered ring;

The subscript n is an integer of from 0 to 3; and each $R^4$ is independently selected from halogen, cyano, nitro, $R^{17}$, $OR^{17}$, $SR^{17}$, $COR^{17}$, $CO_2R^{17}$, $N(R^{17})_2$ and $CON(R^{17})_2$, wherein each $R^{17}$ is independently selected from H, ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl, or two $R^{17}$ groups attached to the same nitrogen atom are combined to form a five- to eight-membered ring.

Also included in this aspect of the invention are any pharmaceutically acceptable salts of the above compounds.

A number of groups of embodiments are preferred. In one group of preferred embodiments, $R^1$ is selected from

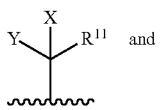
(Ia)

and

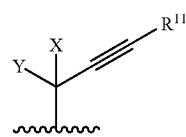
(Ib)

In another group of preferred embodiments, wherein X is OH; more preferably, X is OH, and $R^1$ is selected from

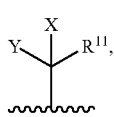
(Ia)

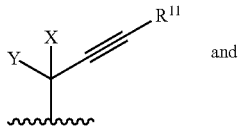
(Ib)

and

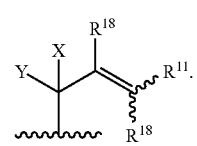
(Ic)

In yet another group of preferred embodiments, X is H, and $R^1$ is selected from

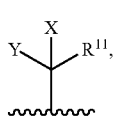
(Ia)

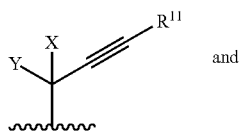
(Ib)

and

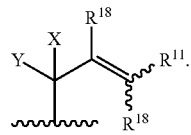
(Ic)

In each of the groups of embodiments above, additional groups are still further preferred. Accordingly, the preferred groups groups below are applicable to each of the above.

In a further group of preferred embodiments, $R^1$ is

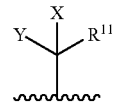
(Ia)

wherein $R^{11}$ is preferably selected from the group consisting of pyrrolyl, imidazolyl, thiazolyl, oxazolyl, isoxazolyl, triazolyl, pyrazolyl, benzimidazolyl, benzthiazolyl, indolyl, thienyl, furyl, pyridyl, quinolinyl, isoquinolinyl, quinoxalinyl, pyrimidinyl, pyrazinyl and pyridazinyl. Each of the recited heteroaryl groups is optionally substituted as described above. More preferably, $R^{11}$ is selected from the group consisting of pyrrolyl, imidazolyl, thiazolyl, oxazolyl, isoxazolyl, triazolyl and pyrazolyl, still more preferably, pyrrolyl. In the most preferred embodiments, $R^{11}$ is pyrrolyl, optionally substituted with from one to two substituents independently selected from the group consisting of halogen, cyano, nitro, ($C_1$-$C_8$)alkyl, ($C_2$-$C_8$)heteroalkyl, ($C_1$-$C_8$)haloalkyl, phenyl($C_1$-$C_6$)alkyl and phenyl($C_2$-$C_6$)heteroalkyl. Still further preferred, are those embodiments in which $R^2$ is selected from H, ($C_1$-$C_8$)alkyl, ($C_3$-$C_8$)cycloalkyl and ($C_4$-$C_8$)cycloalkyl-alkyl, wherein any alkyl portions of $R^2$ are optionally substituted with from one to three substituents independently selected from halogen, nitro, cyano, hydroxy, oxo and amino. In yet further preferred embodiments, $R^3$ is selected from phenyl, pyridyl, thienyl and thiazolyl, optionally substituted with from one to five substituents independently selected from halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl, or two $R^{16}$ groups attached to the same nitrogen atom are combined to form a five- to eight-membered ring. In further preferred embodiments, the subscript n is an integer of from 0 to 2, and each $R^4$ is independently selected from the group consisting of halogen, ($C_1$-$C_8$)alkyl and halo($C_1$-$C_8$)alkyl.

In another group of preferred embodiments, $R^1$ has the formula:

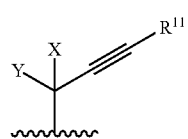

(Ib)

wherein $R^{11}$ is preferably selected from the group consisting of pyrrolyl, imidazolyl, thiazolyl, oxazolyl, isoxazolyl, triazolyl, pyrazolyl, benzimidazolyl, benzthiazolyl, indolyl, thienyl, furyl, pyridyl, quinolinyl, isoquinolinyl, quinoxalinyl, pyrimidinyl, pyrazinyl and pyridazinyl. Each of the recited heteroaryl groups is optionally substituted as described above. More preferably, $R^{11}$ is selected from the group consisting of pyrrolyl, imidazolyl, thiazolyl, oxazolyl, isoxazolyl, triazolyl and pyrazolyl, still more preferably, pyrrolyl. In the most preferred embodiments, $R^{11}$ is pyrrolyl, optionally substituted with from one to two substituents independently selected from the group consisting of halogen, cyano, nitro, $(C_1-C_8)$alkyl, $(C_2-C_8)$heteroalkyl, $(C_1-C_8)$haloalkyl, phenyl$(C_1-C_6)$alkyl and phenyl$(C_2-C_6)$heteroalkyl. Still further preferred, are those embodiments in which $R^2$ is selected from H, $(C_1-C_8)$alkyl, $(C_3-C_8)$cycloalkyl and $(C_4-C_8)$cycloalkyl-alkyl, wherein any alkyl portions of $R^2$ are optionally substituted with from one to three substituents independently selected from halogen, nitro, cyano, hydroxy, oxo and amino. In yet further preferred embodiments, $R^3$ is selected from phenyl, pyridyl, thienyl and thiazolyl, optionally substituted with from one to five substituents independently selected from halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl$(C_1-C_8)$alkyl, and phenyl$(C_2-C_8)$heteroalkyl; wherein each $R^{16}$ is independently selected from $(C_1-C_8)$alkyl, $(C_3-C_8)$alkenyl, $(C_3-C_8)$alkynyl, $(C_2-C_8)$heteroalkyl and halo$(C_1-C_8)$alkyl, or two $R^{16}$ groups attached to the same nitrogen atom are combined to form a five- to eight-membered ring. In further preferred embodiments, the subscript n is an integer of from 0 to 2, and each $R^4$ is independently selected from the group consisting of halogen, $(C_1-C_8)$alkyl and halo$(C_1-C_8)$alkyl.

In another group of preferred embodiments, $R^1$ has the formula:

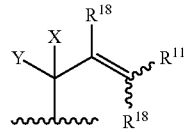

(Ic)

wherein $R^{11}$ is preferably selected from the group consisting of pyrrolyl, imidazolyl, thiazolyl, oxazolyl, isoxazolyl, triazolyl, pyrazolyl, benzimidazolyl, benzthiazolyl, indolyl, thienyl, furyl, pyridyl, quinolinyl, isoquinolinyl, quinoxalinyl, pyrimidinyl, pyrazinyl and pyridazinyl. Each of the recited heteroaryl groups is optionally substituted as described above. More preferably, $R^{11}$ is selected from the group consisting of pyrrolyl, imidazolyl, thiazolyl, oxazolyl, isoxazolyl, triazolyl and pyrazolyl, still more preferably, pyrrolyl. In the most preferred embodiments, $R^{11}$ is pyrrolyl, optionally substituted with from one to two substituents independently selected from the group consisting of halogen, cyano, nitro, $(C_1-C_8)$alkyl, $(C_2-C_8)$heteroalkyl, $(C_1-C_8)$haloalkyl, phenyl$(C_1-C_6)$alkyl and phenyl$(C_2-C_6)$heteroalkyl. Still further preferred, are those embodiments in which $R^2$ is selected from H, $(C_1-C_8)$alkyl, $(C_3-C_8)$cycloalkyl and $(C_4-C_8)$cycloalkyl-alkyl, wherein any alkyl portions of $R^2$ are optionally substituted with from one to three substituents independently selected from halogen, nitro, cyano, hydroxy, oxo and amino. In yet further preferred embodiments, $R^3$ is selected from phenyl, pyridyl, thienyl and thiazolyl, optionally substituted with from one to five substituents independently selected from halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl$(C_1-C_8)$alkyl, and phenyl$(C_2-C_8)$heteroalkyl; wherein each $R^{16}$ is independently selected from $(C_1-C_8)$alkyl, $(C_3-C_8)$alkenyl, $(C_3-C_8)$alkynyl, $(C_2-C_8)$heteroalkyl and halo$(C_1-C_8)$alkyl, or two $R^{16}$ groups attached to the same nitrogen atom are combined to form a five- to eight-membered ring. In further preferred embodiments, the subscript n is an integer of from 0 to 2, and each $R^4$ is independently selected from the group consisting of halogen, $(C_1-C_8)$alkyl and halo$(C_1-C_8)$alkyl.

In a related aspect, the present invention provides compounds having the formula:

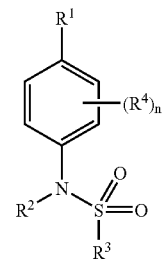

(I)

wherein $R^1$ is selected from:

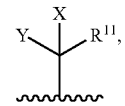

Ia

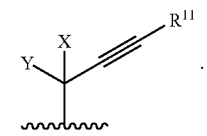

Ib

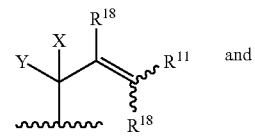

Ic and

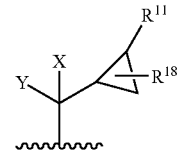

Id wherein $R^{11}$ is selected from halogen, nitro, cyano, $R^{12}$, $OR^{12}$, $SR^{12}$, $NHR^{12}$, $N(R^{12})_2$, $(C_4-C_8)$cycloalkyl, $(C_5-C_8)$ cycloalkenyl, COR$^{12}$, CO$_2$R$^{12}$, CONHR$^{12}$, CON(R$^{12}$)$_2$, aryl, aryl(C$_1$-C$_4$)alkyl, heteroaryl and heteroaryl(C$_1$-C$_4$)alkyl; wherein each R$^{12}$ is (C$_1$-C$_8$)alkyl, (C$_3$-C$_8$)alkenyl, (C$_3$-C$_8$) alkynyl, (C$_2$-C$_8$)heteroalkyl, halo(C$_1$-C$_8$)alkyl or two R$^{12}$ groups attached to the same nitrogen atom are combined to form a five- to eight-membered ring and any alkyl portions of R$^{11}$ are optionally substituted with from one to three substituents independently selected from halogen, OR$^{13}$, NHSO$_2$R$^{14}$ and NHC(O)R$^{13}$, and any aryl or heteroaryl portions of R$^{11}$ are optionally substituted with from one to five substituents independently selected from halogen, cyano, nitro, R$^{14}$, OR$^{13}$, SR$^{13}$, N(R$^{13}$)$_2$, NHSO$_2$R$^{14}$, NHC(O)R$^{13}$, phenyl, phenyl(C$_1$-C$_8$)alkyl, and phenyl(C$_2$-C$_8$)heteroalkyl; wherein each R$^{13}$ is independently selected from H, (C$_1$-C$_8$)alkyl, (C$_3$-C$_8$)alkenyl, (C$_3$-C$_8$)alkynyl, (C$_2$-C$_8$)heteroalkyl and halo (C$_1$-C$_8$)alkyl and each R$^{14}$ is independently selected from (C$_1$-C$_8$)alkyl, (C$_3$-C$_8$)alkenyl, (C$_3$-C$_8$)alkynyl, (C$_2$-C$_8$)heteroalkyl and halo(C$_1$-C$_8$)alkyl. Optionally, R$^{11}$ is combined with either X or Y to form a five- to six-membered monocyclic or fused bicyclic ring containing from 0 to 3 heteroatoms selected from N, O and S. Each R$^{18}$ is independently selected from the group consisting of H, (C$_1$-C$_8$)alkyl, (C$_2$-C$_8$)heteroalkyl, halo(C$_1$-C$_8$)alkyl, aryl and heteroaryl. Additionally, when R$^1$ is a group of formula Ia, R$^{11}$ is other than (C$_1$-C$_3$) alkyl and halo(C$_1$-C$_3$)alkyl.

In each of the R$^1$ groups above, the component X represents H, NH$_2$, NHR$^{15}$, NHSO$_2$R$^{15}$, OH or OR$^{15}$, wherein R$^{15}$ is (C$_1$-C$_8$)alkyl, (C$_3$-C$_8$)alkenyl, (C$_3$-C$_8$)alkynyl, (C$_2$-C$_8$)heteroalkyl or halo(C$_1$-C$_8$)alkyl; and Y is fluoro(C$_1$-C$_4$)alkyl. In particularly preferred embodiments, Y is CF$_3$.

Returning to formula I, R$^2$ is selected from H, (C$_1$-C$_8$) alkyl, (C$_2$-C$_8$)heteroalkyl, (C$_3$-C$_8$)alkenyl, (C$_3$-C$_8$)alkynyl, (C$_3$-C$_8$)cycloalkyl and (C$_4$-C$_8$)cycloalkyl-alkyl, wherein any alkyl portions of R$^2$ are optionally substituted with from one to three substituents independently selected from halogen, nitro, cyano, hydroxy, oxo and amino; and R$^3$ is selected from aryl and heteroaryl, the aryl or heteroaryl group being optionally substituted with from one to five substituents independently selected from halogen, cyano, nitro, R$^{16}$, OR$^{16}$, SR$^{16}$, COR$^{16}$, CO$_2$R$^{16}$, NHR$^{16}$, N(R$^{16}$)$_2$, CONHR$^{16}$, CON(R$^{16}$)$_2$, NHSO$_2$R$^{16}$, NHC(O)R$^{16}$, phenyl, phenyl(C$_1$-C$_8$)alkyl, and phenyl(C$_2$-C$_8$)heteroalkyl; wherein each R$^{16}$ is independently selected from (C$_1$-C$_8$)alkyl, (C$_3$-C$_8$)alkenyl, (C$_3$-C$_8$) alkynyl, (C$_2$-C$_8$)heteroalkyl and halo(C$_1$-C$_8$)alkyl, or two R$^{16}$ groups attached to the same nitrogen atom are combined to form a five- to eight-membered ring. Optionally, R$^2$ and R$^4$ are combined to form a five- to six-membered fused ring containing from 1 to 3 heteroatoms selected from N, O and S.

The subscript n is an integer of from 0 to 3, indicating the presence or absence of substituents on the phenyl ring core of formula I. Each of the R$^4$ substituents is independently selected from halogen, cyano, nitro, R$^{17}$, OR$^{17}$, SR$^{17}$, COR$^{17}$, CO$_2$R$^{17}$, N(R$^{17}$)$_2$ and CON(R$^{17}$)$_2$, wherein each R$^{17}$ is independently selected from H, (C$_1$-C$_8$)alkyl, (C$_3$-C$_8$)alkenyl, (C$_3$-C$_8$)alkynyl, (C$_2$-C$_8$)heteroalkyl or halo(C$_1$-C$_8$)alkyl, or two R$^{17}$ groups attached to the same nitrogen atom are combined to form a five- to eight-membered ring.

In addition to the compounds provided in formula I, pharmaceutically acceptable salts thereof are also provided.

In one group of preferred embodiments, R$^1$ is selected from

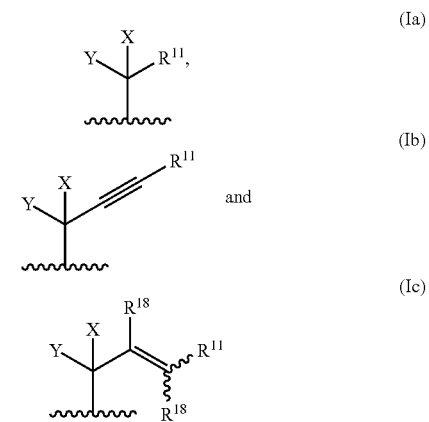

and X is OH.

In another group of preferred embodiments, R$^1$ is selected from

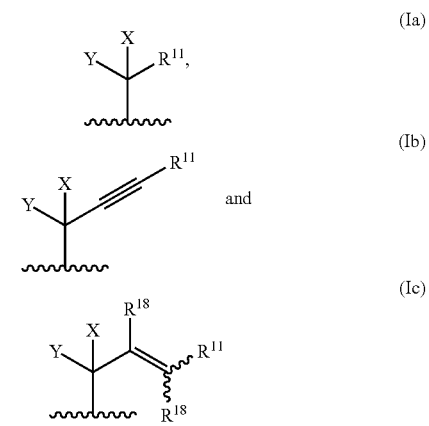

and X is H.

Within each of these groups of preferred embodiments are several further preferred groups. Accordingly, in the discussion below, preferred embodiments are provided in which X is H or X is OH.

In one of these groups, R$^1$ is

wherein R$^{11}$ is selected from phenyl, pyridyl, pyridazinyl, imidazolyl, thiazolyl, oxazolyl, pyrrolyl, tetrazolyl, indolyl, benzimidazolyl, benzothienyl and benzothiazolyl, each of these R$^{11}$ groups being optionally substituted with from one to five substituents independently selected from halogen, (C$_1$-C$_8$)alkyl, (C$_3$-C$_8$)alkenyl, (C$_3$-C$_8$)alkynyl, (C$_2$-C$_8$)heteroalkyl, (C$_1$-C$_8$)haloalkyl, phenyl(C$_1$-C$_6$)alkyl and phenyl (C$_2$-C$_6$)heteroalkyl. In particularly preferred embodiments, Y is CF$_3$.

In still further preferred embodiments, R$^1$ is a group of formula Ia in which R$^{11}$ is phenyl, optionally substituted with from one to two substituents independently selected from the group consisting of halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. The remaining groups $R^2$, $R^3$ and $R^4$ also have certain preferred members. In particular, $R^2$ is preferably selected from H, $(C_1-C_8)$alkyl, $(C_3-C_8)$cycloalkyl and $(C_4-C_8)$cycloalkyl-alkyl, wherein any alkyl portions of $R^2$ are optionally substituted with from one to three substituents independently selected from halogen, nitro, cyano, hydroxy, oxo and amino. $R^3$ is preferably selected from phenyl, pyridyl, thienyl and thiazolyl, optionally substituted with from one to five substituents independently selected from the group consisting of halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl$(C_1-C_8)$alkyl, and phenyl$(C_2-C_8)$heteroalkyl; wherein each $R^{16}$ is independently selected from $(C_1-C_8)$alkyl, $(C_3-C_8)$alkenyl, $(C_3-C_8)$alkynyl, $(C_2-C_8)$heteroalkyl and halo$(C_1-C_8)$alkyl, or two $R^{16}$ groups attached to the same nitrogen atom are combined to form a five- to eight-membered ring. The subscript n is preferably 0, 1, or 2 and each $R^4$ is preferably selected from halogen, $(C_1-C_8)$alkyl and halo$(C_1-C_8)$alkyl.

In another group of still further preferred embodiments, $R^1$ is a group of formula Ia in which $R^{11}$ is pyrrolyl, optionally substituted with from one to two substituents independently selected from halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. Preferred members of the remaining groups $R^2$, $R^3$ and $R^4$ are the same as have been described above for the embodiments in which $R^{11}$ is phenyl.

Another group of preferred embodiments are those compounds of formula I in which $R^1$ is

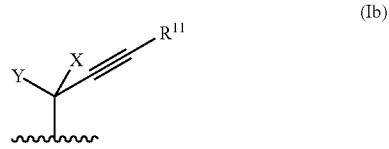

(Ib)

wherein $R^{11}$ is selected from phenyl, pyridyl, pyridazinyl, imidazolyl, thiazolyl, oxazolyl, pyrrolyl, tetrazolyl, indolyl, benzimidazolyl, benzothienyl and benzothiazolyl, each of these $R^{11}$ groups being optionally substituted with from one to five substituents independently selected from halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. In particularly preferred embodiments, Y is $CF_3$.

In still further preferred embodiments, $R^1$ is a group of formula Ib in which $R^{11}$ is phenyl, optionally substituted with from one to two substituents independently selected from the group consisting of halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. The remaining groups $R^2$, $R^3$ and $R^4$ also have certain preferred members. In particular, $R^2$ is preferably selected from H, $(C_1-C_8)$alkyl, $(C_3-C_8)$cycloalkyl and $(C_4-C_8)$cycloalkyl-alkyl, wherein any alkyl portions of $R^2$ are optionally substituted with from one to three substituents independently selected from halogen, nitro, cyano, hydroxy, oxo and amino. $R^3$ is preferably selected from phenyl, pyridyl, thienyl and thiazolyl, optionally substituted with from one to five substituents independently selected from the group consisting of halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl$(C_1-C_8)$alkyl, and phenyl$(C_2-C_8)$heteroalkyl; wherein each $R^{16}$ is independently selected from $(C_1-C_8)$alkyl, $(C_3-C_8)$alkenyl, $(C_3-C_8)$alkynyl, $(C_2-C_8)$heteroalkyl and halo$(C_1-C_8)$alkyl, or two $R^{16}$ groups attached to the same nitrogen atom are combined to form a five- to eight-membered ring. The subscript n is preferably 0, 1, or 2 and each $R^4$ is preferably selected from halogen, $(C_1-C_8)$alkyl and halo$(C_1-C_8)$alkyl.

In another group of still further preferred embodiments, $R^1$ is a group of formula Ib in which $R^{11}$ is pyridyl, optionally substituted with from one to two substituents independently selected from halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. Preferred members of the remaining groups $R^2$, $R^3$ and $R^4$ are the same as have been described above for the embodiments in which $R^{11}$ is phenyl.

In yet another group of still further preferred embodiments, $R^1$ is a group of formula Ib in which $R^{11}$ is pyridazinyl or pyrrolyl, optionally substituted with from one to two substituents independently selected from halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. Preferred members of the remaining groups $R^2$, $R^3$ and $R^4$ are the same as have been described above for the embodiments in which $R^{11}$ is phenyl.

Still another group of preferred embodiments are those compounds of formula I in which $R^1$ is

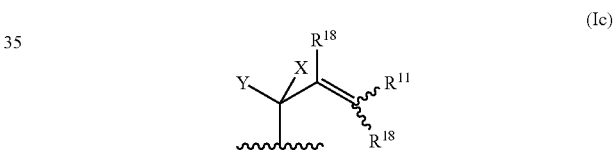

(Ic)

wherein $R^{11}$ is selected from phenyl, pyrrolyl, pyridyl and pyridazinyl, each of these $R^{11}$ groups being optionally substituted with from one to five substituents independently selected from halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. In particularly preferred embodiments, Y is $CF_3$.

In still further preferred embodiments, $R^1$ is a group of formula Ic in which $R^{11}$ is phenyl, optionally substituted with from one to two substituents independently selected from the group consisting of halogen, $(C_1-C_8)$alkyl, $(C_3-C_8)$alkenyl, $(C_3-C_8)$alkynyl, $(C_2-C_8)$heteroalkyl, $(C_1-C_8)$haloalkyl, phenyl$(C_1-C_6)$alkyl and phenyl$(C_2-C_6)$heteroalkyl. The remaining groups $R^2$, $R^3$ and $R^4$ also have certain preferred members. In particular, $R^2$ is preferably selected from H, $(C_1-C_8)$alkyl, $(C_3-C_8)$cycloalkyl and $(C_4-C_8)$cycloalkyl-alkyl, wherein any alkyl portions of $R^2$ are optionally substituted with from one to three substituents independently selected from halogen, nitro, cyano, hydroxy, oxo and amino. $R^3$ is preferably selected from phenyl, pyridyl, thienyl and thiazolyl, optionally substituted with from one to five substituents independently selected from the group consisting of halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl$(C_1-C_8)$alkyl, and phenyl$(C_2-C_8)$heteroalkyl; wherein each $R^{16}$ is independently selected from $(C_1-C_8)$ alkyl, $(C_3-C_8)$alkenyl, $(C_3-C_8)$alkynyl, $(C_2-C_8)$heteroalkyl and halo$(C_1-C_8)$alkyl, or two $R^{16}$ groups attached to the same nitrogen atom are combined to form a five- to eight-membered ring. The subscript n is preferably 0, 1, or 2 and each $R^4$ is preferably selected from halogen, $(C_1-C_8)$alkyl and halo $(C_1-C_8)$alkyl.

The most preferred compounds of the present invention are those provided in the Examples below.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3$H (tritium) and $^{14}$C (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

In another aspect of the invention, pharmaceutical compositions are provided in which a compound of formula I is combined with a pharmaceutically acceptable carrier or diluent. Particular compositions and methods for their use are provided in more detail below.

In yet another aspect, the present invention provides a method for modulating the action of an LXR receptor, preferably LXRα, in a cell. According to this method, the cell is contacted with a sufficient concentration of a composition containing a compound of formula I for either an agonistic or antagonistic effect to be detected. In preferred embodiments, the composition contains an amount of the compound which has been determined to provide a desired therapeutic or prophylactic effect for a given LXR-mediated condition.

In still another aspect, the present invention provides methods for the treatment of pathology such as obesity, diabetes, hypercholesterolemia, atherosclerosis, and hyperlipoproteinemia using pharmaceutical compositions containing compounds of the foregoing description of the general Formula I. Briefly, this aspect of the invention involves administering to a patient an effective formulation of one or more of the subject compositions. In other embodiments, the compound of Formula I can be administered in combination with other anti-hypercholesterolemic agents (e.g., a bile acid sequestrant, nicotinic acid, fibric acid derivatives or HMG CoA reductase inhibitors), or in combination with other agents that affect cholesterol or lipid metabolism.

Preparation of the Compounds

Several methods for preparing the compounds of the present invention are illustrated in the following schemes and examples. Starting materials are made by known procedures or as illustrated. One of skill in the art will understand that similar methods can be used for the synthesis of the compounds.

As shown in Scheme 1, compounds of the present invention can be prepared beginning with commercially available 1',1',1',4-tetrafluoroacetophenone (1-1). Treatment of 1-1 with an N-substituted arylsulfonamide (1-2) in the presence of a base such as potassium carbonate, cesium carbonate, or sodium hydride in a suitable solvent such as DMF or DMSO provides adduct 1-3. Treatment of 1-3 with organometal species 1-4 provides compounds of formula 1-5.

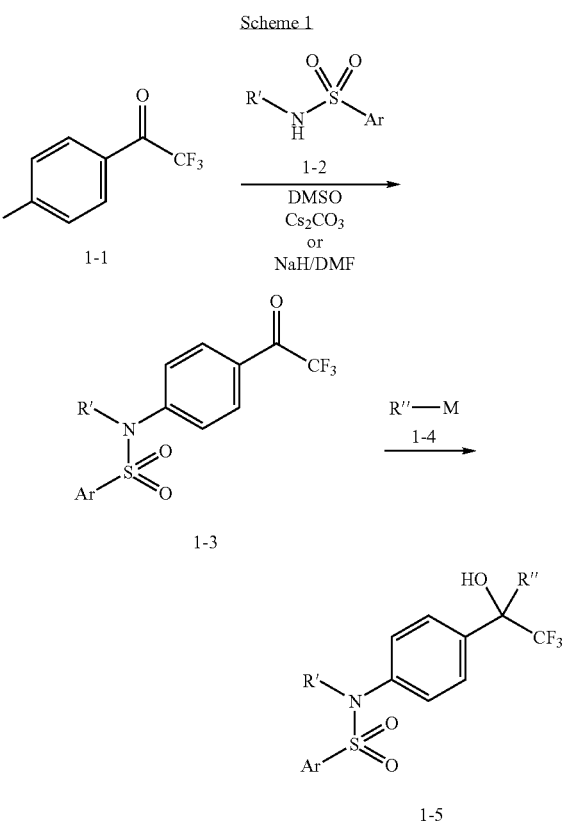

Scheme 1

Examples of suitable organometal compounds are shown in Scheme 2. As illustrated in Scheme 2, a heterocycle, for example, 1-alkylimidazole 2-1, can be lithiated with n-butyllithium in THF or diethylether to give derivative 2-2. Also, bromodifluoroacetate or iododifluoroacetate can be converted into zinc species 2-4 by heating in the presence of zinc powder. An arylhalide or heteroarylhalide (2-5) can be converted to organomagnesium species 2-6 by reaction with magnesium in THF or diethylether or reaction with isopropylmagnesium bromide. In addition, an alkyne can be lithiated with, for example, n-butyllithium in THF, or metalated with isopropylmagnesium bromide in THF.

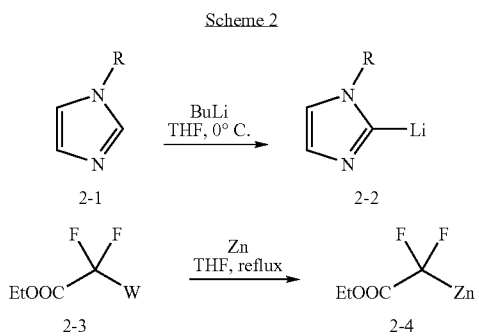

Scheme 2

-continued

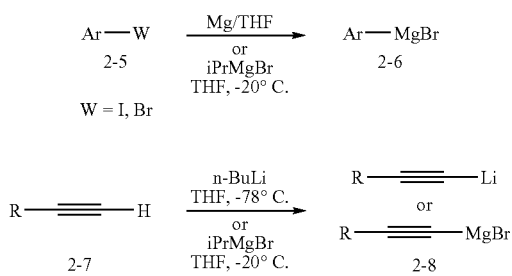

The preparation of intermediate alkynes 2-7 is illustrated in Scheme 3. An alkyl, aryl or heteroaryl halide (3-1) can be coupled to 2-methyl-3-butyn-2-ol according to the procedure described in Bleicher et al. (1995) *Synlett* 1115-1116. Resulting alcohol 3-2, can be converted to alkyne 2-7 using a base such as sodium hydride in a suitable solvent such as toluene, according to the procedure described in Havens et al. (1985) *J. Org. Chem.*, 50:1763-1765.

Alternatively an alkyl, aryl or heteroaryl halide can be coupled to ethynyltrimethylsilane via a Palladium mediated reaction to afford 3-4 (see, e.g., R. C. Larock; *Comprehensive Organic Transformations*, $2^{nd}$ ed., John Wiley & Sons, New York, pp. 596599, (1999)). Subsequent treatment of 3-4 with, for example, potassium carbonate in anhydrous methanol gives alkyne 2-7.

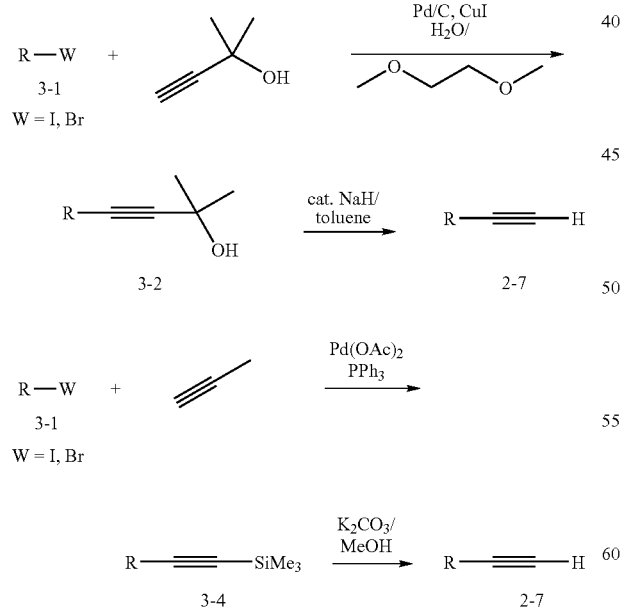

An alternative preparation of the compounds of the present invention is shown in Scheme 4.

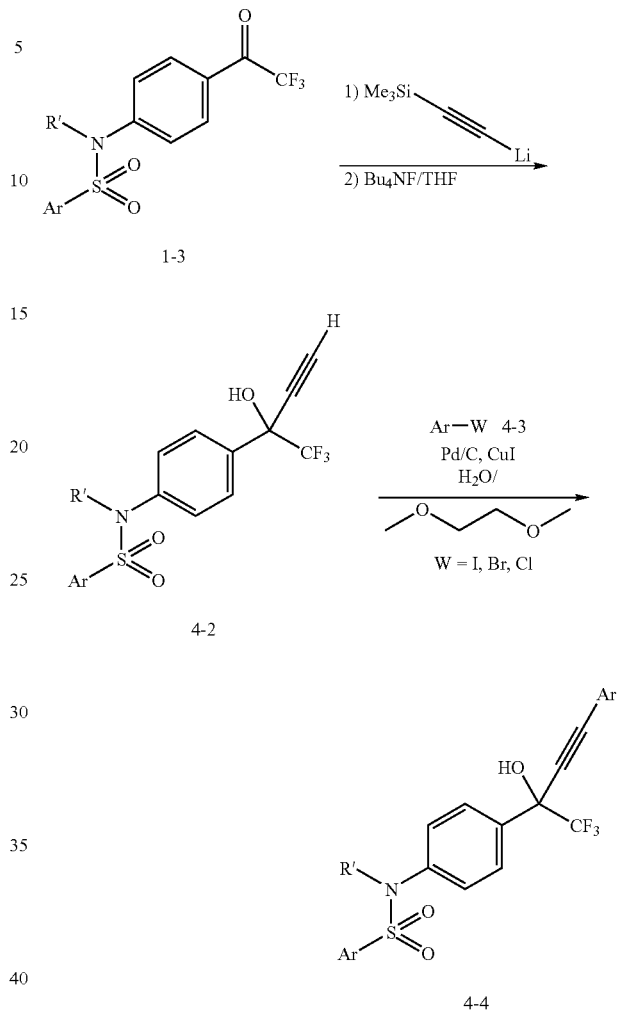

Trimethylsilyl-ethynyl lithium is added to 1-3 and the adduct subsequently treated with tetrabutyl ammonium fluoride in THF to give ethynyl derivative 4-2. This derivative can be reacted with an alkyl, aryl or heteroaryl halide using the procedure described by Bleicher et al. (1995) *Synlett*, 1115-1116 or a similar Palladium mediated coupling reaction (see, e.g., R. C. Larock; Comprehensive Organic Transformations, $2^{nd}$ ed., John Wiley & Sons, New York, pp. 596-599, (1999)) to afford 4-4.

Another alternative synthesis of the compounds of the present invention is shown in Scheme 5. A haloaniline (5-1) can be alkylated, acylated or arylated (general addition of R-group) to form 5-2. 5-2 can be sulfonylated with, for example, an appropriate sulfonyl halide (5-3) to form 5-4. Halo-substituted arylsulfonamide 5-4 can be converted to alcohol 5-7 upon treatment with t-butyllithium followed by ketone 5-5. Alternatively, 5-2 can be converted to 5-6 upon treatment with t-butyllithium followed by ketone 5-5. Alcohol 5-6 can be sulfonylated to form compounds of formula 5-7.

Scheme 5

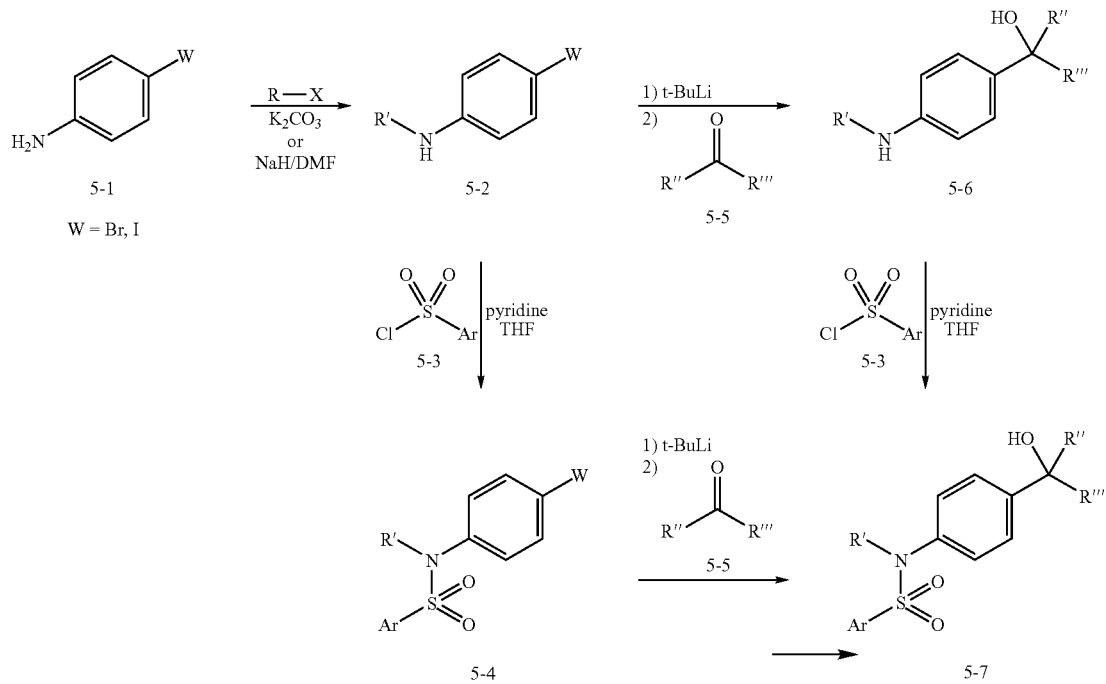

The synthesis of compounds possessing the general formula 6-4 is shown in Scheme 6. Halo-substituted arylsulfonamide 5-4 can be converted into fluoroketone 6-3 upon treatment with t-butyllithium followed by addition of α,α-difluoroester 6-2. Subsequent treatment of 6-3 with CF$_3$—TMS in the presence of tetrabutylammonium fluoride in THF (see, e.g., G. K. S. Prakash in *Synthetic Fluorine Chemistry;* G. A. Olah et al., Eds. John Wiley; New York, 1992; Chapter 10) provides compounds of formula 6-4.

Scheme 6

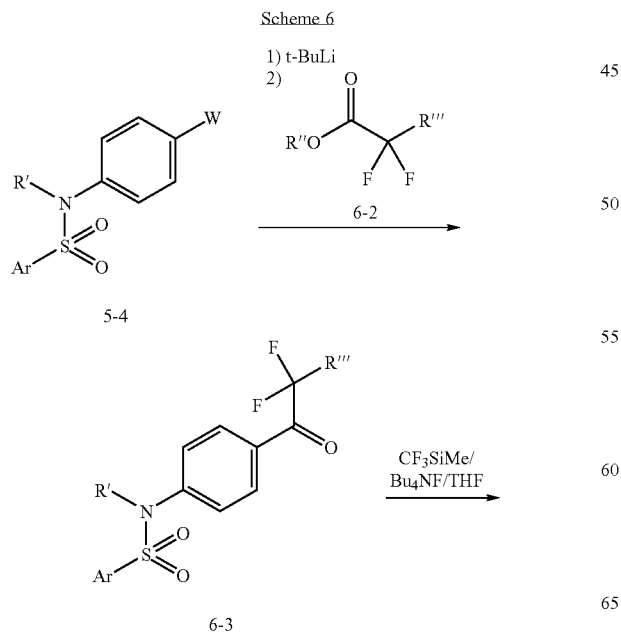

-continued

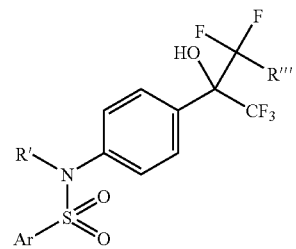

Preparation of intermediate α,α-difluoroester 6-2 can be accomplished by a variety of methods, including the methods illustrated in Scheme 7. Ketoester 7-1 can be fluorinated with diethylaminosulfur trifluoride (DAST), as reviewed in Middleton (1975) *J. Org. Chem.* 40:574. Acetic acid ester 7-3 can be fluorinated by treatment with a strong base, such as potassium hexamethyldisalazide, followed by addition of a suitable fluorinating agent, such as 7-4 (see, e.g., Differding et al. (1991) *Tetrahedron Lett.* 32:1779). Alternatively, an aryl iodide or aryl bromide can be treated with ethyl bromodifluoroacetate (7-5) in the presence of copper metal to provide 7-6 (see, e.g., Eto et al. (2000) *Chem. Pharm. Bull.* 48:982).

Scheme 7

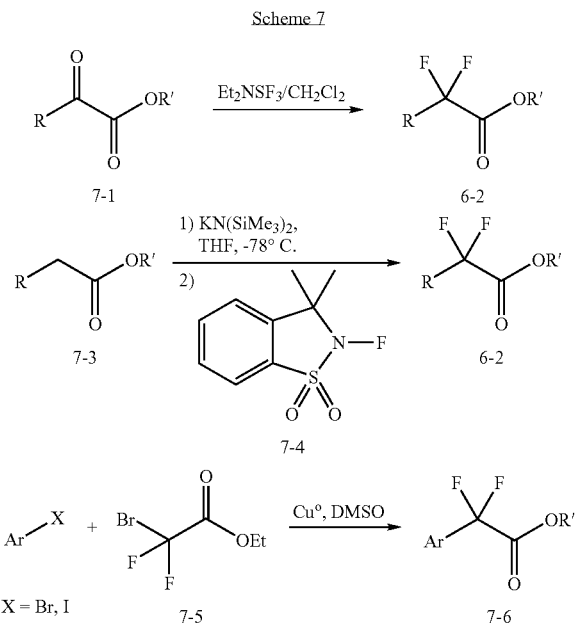

As shown in Scheme 8, alcohols 5-7 can be alkylated in the presence of a base such as sodium hydride in a suitable solvent such as THF or DMF to give ethers 8-2 or deoxygenated to give 8-3 by using, e.g., triethylsilane and $BF_3 \cdot OEt_2$.

Scheme 8

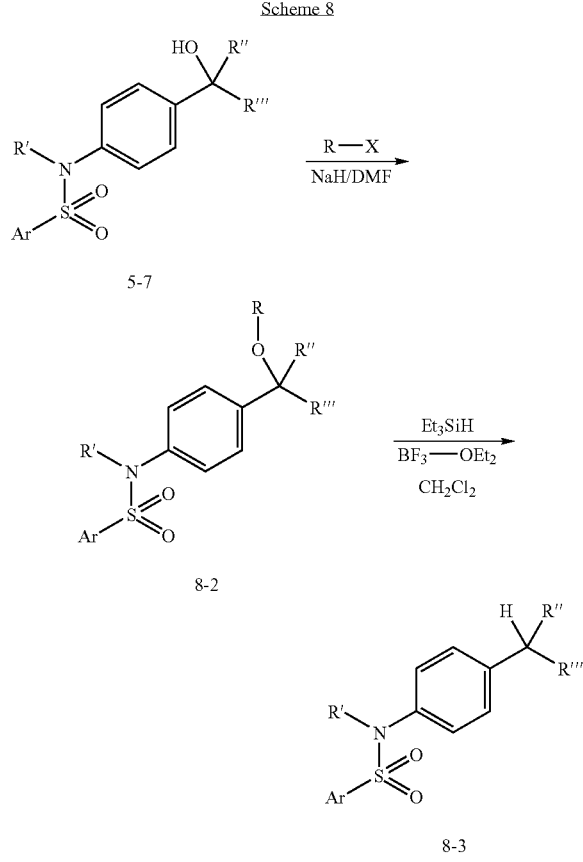

Analysis of Compounds

Representative compounds and compositions were demonstrated to have pharmacological activity in in vitro and in vivo assays, e.g., they are capable of specifically modulating a cellular physiology to reduce an associated pathology or provide or enhance a prophylaxis.

Certain preferred compounds and compositions are capable of specifically regulating LXR. Compounds may be evaluated in vitro for their ability to activate LXR receptor function using biochemical assays (see co-pending applications Ser. No. 08/975,614 (filed Nov. 21, 1997) and Ser. No. 09/163,713 (filed Sep. 30, 1998)), or in cell-based assays such as that described in Lehmann, et al. (*J. Biol. Chem.* 1997, 272(6), 3137-3140). Alternatively, the compounds and compositions can be evaluated for their ability to increase or decrease gene expression modulated by LXR, using western-blot analysis. Established animal models to evaluate hypocholesterolemic effects of the compounds are also known in the art. For example, compounds disclosed herein can lower cholesterol levels in hamsters fed a high-cholesterol diet, using a protocol similar to that described in Spady et al. (*J. Clin. Invest.* 1988, 81, 300), Evans et al. (*J. Lipid Res.* 1994, 35, 1634), and Lin et al (*J. Med. Chem.* 1995, 38, 277). Still further, LXRα animal models (e.g., LXRα (±) and (−/−) mice) can be used for evaluation of the present compounds and compositions (see, for example, Peet, et al. *Cell* 1998, 93, 693-704).

Accordingly, as used herein, the term "LXR-modulating amount" refers to that amount of a compound that is needed to produce a desired effect in any one of the cell-based assays, biochemical assays or animal models described above. Typically, an LXR-modulating amount of a compound will be at least that amount which exhibits an $EC_{50}$ in a reporter-gene cell-based assay (relative to an untreated control).

Formulation and Administration of Compounds and Pharmaceutical Compositions

The invention provides methods of using the subject compounds and compositions to treat disease or provide medicinal prophylaxis, to activate LXR receptor function in a cell, to reduce blood cholesterol concentration in a host, to slow down and/or reduce the abnormal cellular proliferation including the growth of tumors, etc. These methods generally involve contacting the cell or cells with or administering to a host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic therapeutic or prophylactic agents, different from the subject compounds. In many instances, administration in conjunction with the subject compositions enhances the efficacy of such agents. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to use labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H-NMR spectra were recorded on a Varian Gemini 400 MHz NMR spectrometer. Significant peaks are tabulated and typically include: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). Starting materials in the synthesis examples below are either available from commercial sources such as Aldrich Chemical Co., Milwaukee, Wis., USA, or via literature procedures. Abbreviations used in the examples below have their accepted meanings in the chemical literature. For example, THF (tetrahydrofuran), Et$_2$O (diethyl ether), MeOH (methanol), CH$_2$Cl$_2$ (methylene chloride), LDA (lithium diisopropylamide), MeCN (acetonitrile), and DMAP (4-dimethyaminopyridine).

A number of the compounds provided below were prepared following procedures outlined in U.S. application Ser. No. 10/354,922, now U.S. Pat. No. 7,071,358. Examples 78 and 88, specifically referred to below, are provided as Preparative Examples A and B, respectively.

Example 1

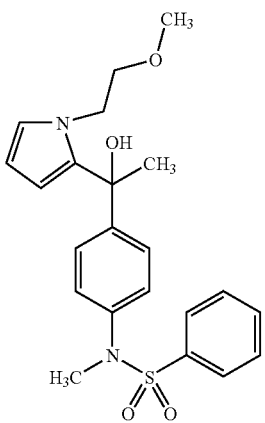

N-(4-{1-Hydroxy-1-[1-(2-methoxyethyl)-1H-pyrrol-2-yl]-ethyl}-phenyl)-N-methyl-benzenesulfonamide The title compound was prepared following a procedure similar to that for Example 78 in U.S. application Ser. No. 10/354,922, now U.S. Pat. No. 7,071,358, and provided below as Preparative Example A.

$^1$H-NMR (CDCl$_3$) δ 6.99 (dd, J=4.0 Hz, 1.7 Hz, 1H), 6.93 (t, J=2.0 Hz, 1H), 6.12 (dd, J=4.0 Hz, 2.6 Hz, 1H), 4.50 (t, J=5.2 Hz, 2H), 3.65 (t, J=5.2 Hz, 2H), 3.28 (s, 3H), 2.42 (s, 3H). Mass Spectrum (ESI) m/e=136.1 (M–31).

The starting material, N-methoxyethyl-2-acetylpyrrole, was prepared using methods similar to those described in Preparative Example A, Step A.

$^1$H-NMR (CDCl$_3$) δ 6.99 (dd, J=4.0 Hz, 1.7 Hz, 1H), 6.93 (t, J=2.0 Hz, 1H), 6.12 (dd, J=4.0 Hz, 2.6 Hz, 1H), 4.50 (t, J=5.2 Hz, 2H), 3.65 (t, J=5.2 Hz, 2H), 3.28 (s, 3H), 2.42 (s, 3H). Mass Spectrum (ESI) m/e=136.1 (M–31).

Example 2

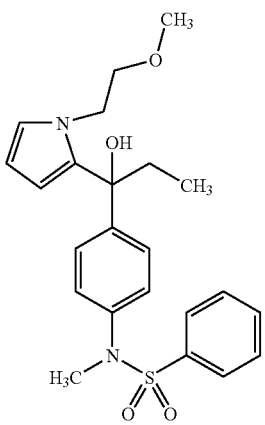

N-(4-{1-Hydroxy-1-[1-(2-methoxyethyl)-1H-pyrrol-2-yl]-propyl}-phenyl)-N-methyl-benzenesulfonamide The title compound was prepared following a procedure similar to that for Example 78 in U.S. application Ser. No. 10/354,922, now U.S. Pat. No. 7,071,358, and provided below as Preparative Example A.

$^1$H-NMR (CDCl$_3$) δ 7.48-7.59 (m, 3H), 7.41 (t, J=7.5 Hz, 2H), 7.19 (d, J=8.6 Hz, 2H), 6.99 (d, J=8.6 Hz, 2H), 6.62 (dd, J=2.7 Hz, 1.9 Hz, 1H), 6.30 (dd, J=3.6 Hz, 1.8 Hz, 1H), 6.15 (t, J=3.2 Hz, 1H), 3.94 (s, 1H), 3.77-3.86 (m, 1H), 3.59-3.67 (m, 1H), 3.33-3.45 (m, 2H), 3.27 (s, 3H), 3.16 (s, 3H), 2.21-2.31 (m, 1H), 2.01-2.11 (m, 1H), 0.80 (t, J=7.4 Hz, 3H). Mass Spectrum (ESI) m/e=451.1 (M+23).

The starting material, N-methoxyethyl-2-propionylpyrrole was prepared as follows:

To a solution of 102 mg (0.61 mmol) of N-methoxyethyl-2-acetylpyrrole in 4.5 mL THF at −78° C. was added dropwise 670 μL (0.67 mmol) of a 1.0 M solution of LHMDS in THF and the resultant mixture was stirred for 30 min. After this time, 57 μL (0.92 mmol) of MeI was added dropwise and the mixture was stirred at −78° C. for 1.5 h, then was warmed to 0° C. and stirred for an additional 45 min. After this time, the reaction mixture was quenched by the addition of a saturated aqueous solution of ammonium chloride and extracted with EtOAc. The combined organic layers were dried over Na$_2$SO$_4$, filtered and the filtrate was concentrated. The residue was purified by chromatography on silica gel (pure hexanes grading to hexanes:EtOAc, 88:12) to give the title compound.

$^1$H-NMR (CDCl$_3$) δ 7.00 (dd, J=4.0 Hz, 1.7 Hz, 1H), 6.92 (t, J=2.1 Hz, 1H), 6.13 (dd, J=4.1 Hz, 2.5 Hz, 1H), 4.50 (t, J=5.1 Hz, 2H), 3.65 (t, J=5.2 Hz, 2H), 3.29 (s, 3H), 2.81 (q, J=7.4 Hz, 2H), 1.17 (t, J=7.4 Hz, 3H). Mass Spectrum (ESI) m/e=150.1 (M−31).

Example 3

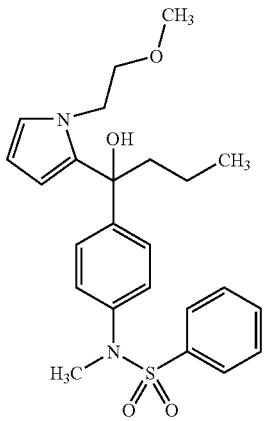

N-(4-{1-Hydroxy-1-[1-(2-methoxyethyl)-1H-pyrrol-2-yl]-butyl}-phenyl)-N-methyl-benzenesulfonamide The title compound was prepared following a procedure similar to that for Example 78 in U.S. application Ser. No. 10/354,922, now U.S. Pat. No. 7,071,358, and provided below as Preparative Example A.

$^1$H-NMR (CDCl$_3$) δ 7.39-7.61 (m, 5H), 7.19 (d, J=8.6 Hz, 2H), 6.99 (d, J=8.5 Hz, 2H), 6.60-6.63 (m, 1H), 6.39-6.42 (m, 1H), 6.15 (t, J=3.1 Hz, 1H), 3.98 (s, 1H), 3.75-3.85 (m, 1H), 3.58-3.67 (m, 1H), 3.31-3.44 (m, 2H), 3.26 (s, 3H), 3.16 (s, 3H), 1.95-2.22 (m, 2H), 1.39-1.56 (m, 1H), 0.90-1.05 (m, 1H), 0.87 (t, J=7.2 Hz, 3H). Mass Spectrum (ESI) m/e=465.2 (M+23).

The starting material, N-methoxyethyl-2-butyrylpyrrole, was prepared as follows:

To a solution of 150 mg (0.90 mmol) of N-methoxyethyl-2-acetylpyrrole in 6 mL THF at −78° C. was added dropwise 990 μL (0.99 mmol) of a 1.0 M solution of LHMDS in THF and the resultant mixture was stirred for 30 min. After this time, 108 μL (1.35 mmol) of EtI was added dropwise and the mixture was warmed to 0° C. and stirred for 2.5 h, then was further warmed to room temperature and stirred for an additional 2.5 h. After this time, 43 μL (0.54 mmol) of EtI was added and the mixture was stirred for an additional 1 h. The reaction mixture was quenched by the addition of a saturated aqueous solution of ammonium chloride and extracted with EtOAc. The combined organic layers were dried over Na$_2$SO$_4$, filtered and the filtrate was concentrated. The residue was purified by chromatography on silica gel (pure hexanes grading to hexanes:EtOAc, 9:1) to give the title compound.

$^1$H-NMR (CDCl$_3$) δ 7.00 (dd, J=4.0 Hz, 1.6 Hz, 1H), 6.92 (t, J=2.0 Hz, 1H), 6.13 (dd, J=4.0 Hz, 2.5 Hz, 1H), 4.50 (t, J=5.1 Hz, 2H), 3.65 (t, J=5.1 Hz, 2H), 3.29 (s, 3H), 2.75 (t, J=7.3 Hz, 2H), 1.67-1.78 (m, 2H), 0.97 (t, J=7.4 Hz, 3H). Mass Spectrum (ESI) m/e=164.1 (M−31).

Example 4

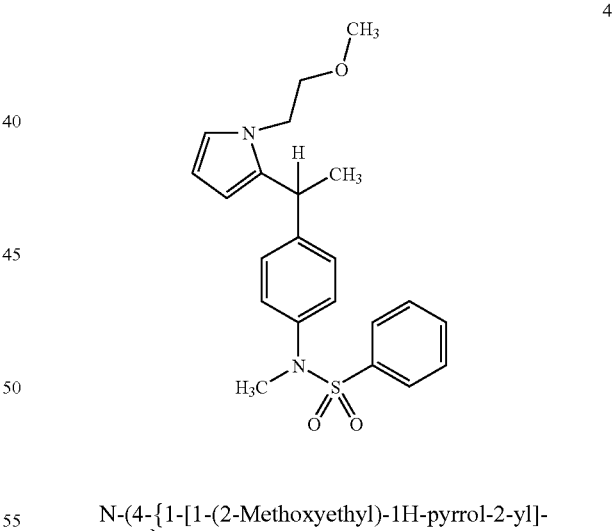

N-(4-{1-[1-(2-Methoxyethyl)-1H-pyrrol-2-yl]-ethyl}-phenyl)-N-methyl-benzenesulfonamide The title compound was prepared from N-(4-{1-hydroxy-1-[1-(2-methox-yethyl)-1H-pyrrol-2-yl]-ethyl}-phenyl)-N-methyl-benzenesulfonamide (Example 1) using triethylsilane and boron trifluoride diethyl etherate as described in Example 88 of U.S. application Ser. No. 10/354,922, now U.S. Pat. No. 7,071,358, and provided below as Preparative Example B.

$^1$H-NMR (CDCl$_3$) δ 7.51-7.60 (m, 3H), 7.43 (t, J=7.8 Hz, 2H), 7.04 (d, J=8.4 Hz, 2H), 6.98 (d, J=8.5 Hz, 2H), 6.65 (s, 1H), 6.13 (t, J=3.4 Hz, 1H), 6.10-6.13 (m, 1H), 4.06-4.13 (m,

1H), 3.68-3.82 (m, 2H), 3.27 (t, J=5.9 Hz, 2H), 3.21 (s, 3H), 3.13 (s, 3H), 1.57 (t, J=7.2 Hz, 3H). Mass Spectrum (ESI) m/e=421.1 (M+23).

Example 5

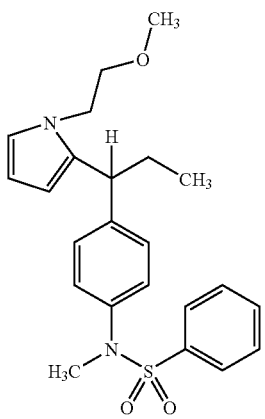

N-(4-{1-[1-(2-Methoxyethyl)-1H-pyrrol-2-yl]-propyl}-phenyl)-N-methyl-benzenesulfonamide The title compound was prepared from N-(4-{1-hydroxy-1-[1-(2-methox-yethyl)-1H-pyrrol-2-yl]-ethyl}-phenyl)-N-methyl-benzenesulfonamide (Example 1) using triethylsilane and boron trifluoride diethyl etherate as described in Example 88 of U.S. application Ser. No. 10/354,922, now U.S. Pat. No. 7,071,358, and provided below as Preparative Example B.

¹H-NMR (CDCl₃) δ 7.00 (dd, J=4.0 Hz, 1.7 Hz, 1H), 6.92 (t, J=2.1 Hz, 1H), 6.13 (dd, J=4.1 Hz, 2.5 Hz, 1H), 4.50 (t, J=5.1 Hz, 2H), 3.65 (t, J=5.2 Hz, 2H), 3.29 (s, 3H), 2.81 (q, J=7.4 Hz, 2H), 1.17 (t, J=7.4 Hz, 3H). Mass Spectrum (ESI) m/e=150.1 (M−31).

Example 6

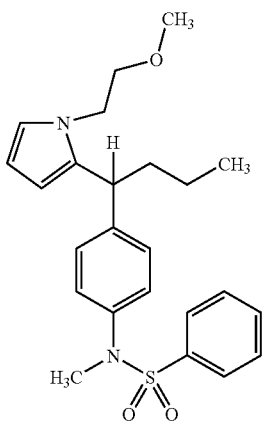

N-(4-{1-[1-(2-Methoxyethyl)-1H-pyrrol-2-yl]-butyl}-phenyl)-N-methyl-benzenesulfonamide The title compound was prepared from N-(4-{1-hydroxy-1-[1-(2-methox-yethyl)-1H-pyrrol-2-yl]-ethyl}-phenyl)-N-methyl-benzenesulfonamide (Example 1) using triethylsilane and boron trifluoride diethyl etherate as described in Example 88 of U.S. application Ser. No. 10/354,922, now U.S. Pat. No. 7,071,358, and provided below as Preparative Example B.

¹H-NMR (CDCl₃) δ 7.50-7.61 (m, 3H), 7.40-7.47 (m, 2H), 7.05 (d, J=8.5 Hz, 2H), 6.97 (d, J=8.4 Hz, 2H), 6.62 (t, J=2.2 Hz, 1H), 6.10-6.17 (m, 2H), 3.71-3.92 (m, 3H), 3.25 (t, J=6.2 Hz, 2H), 3.21 (s, 3H), 3.13 (s, 3H), 1.96-2.07 (m, 1H), 1.74-1.86 (m, 1H), 1.21-1.42 (m, 2H), 0.91 (t, J=7.3 Hz, 3H). Mass Spectrum (ESI) m/e=449 (M+23).

Example 7

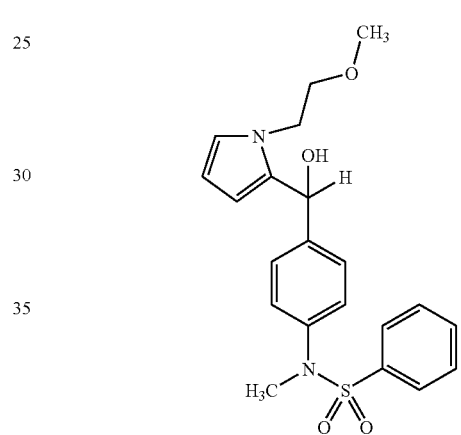

N-(4-{1-Hydroxy-1-[1-(2-methoxyethyl)-1H-pyrrol-2-yl]-methyl}-phenyl)-N-methyl-benzenesulfonamide Step A. N-Methoxyethylpyrrole-2-carboxaldehyde To a suspension of 450 mg (11.25 mmol) of NaH (60% dispersion in mineral oil) in 30 mL DMF at 0° C. was added 990 mg (10.41 mmol) of pyrrole-2-carboxaldehyde and the mixture was stirred at 0° C. for 1.5 h. After this time, 1.03 mL (10.96 mmol) of 2-bromomethyl methyl ether was added and the mixture was warmed to 50° C. and stirred for 2.75 h. The reaction mixture was allowed to cool to room temperature, quenched by the addition of a saturated aqueous solution of ammonium chloride, and extracted with EtOAc. The organic layer was washed with water and brine, dried over Na₂SO₄, filtered and the filtrate was concentrated. The residue was purified by chromatography on silica gel (hexanes:EtOAc, 9:1) to give the title compound.

¹H-NMR (CDCl₃) δ 9.53 (d, J=1.0 Hz, 1H), 7.03 (s,§1H), 6.95 (dd, J=4.0 Hz, 1.7 Hz, 1H), 6.23 (dd, J=4.0 Hz, 2.5 Hz, 1H), 4.50 (t, J=5.1 Hz, 2H), 3.66 (t, J=5.1 Hz, 2H), 3.29 (s, 3H). Mass Spectrum (ESI) m/e=122 (M−31).

Step B. N-(4-{1-Hydroxy-1-[1-(2-methoxyethyl)-1H-pyrrol-2-yl]-methyl}-phenyl)-N-methyl-benzenesulfonamide To a solution of 1.49 g (4.59 mmol) of N-(4-bromophenyl)-N-methyl benzenesulfonamide (see Preparative Example A, Step C) in 37.5 mL THF at −78° C. was added dropwise 5.94 mL (10.10 mmol) of a 1.7 M solution of tert-BuLi in pentane and the resultant mixture was stirred at −78° C. for 15 min. To this mixture was then added a solution of 1.01 g (6.59 mmol) of N-methoxyethylpyrrole-2-carboxaldehyde in 6 mL THF and the mixture was allowed to gradually warm to −30° C. over a 4 h period. After this time, the reaction mixture was quenched by the addition of a saturated aqueous solution of ammonium chloride and extracted with EtOAc. The combined organic layers were dried over $Na_2SO_4$, filtered and the filtrate was concentrated. The residue was purified by chromatography on silica gel (hexanes:EtOAc, 13:7) to give the title compound.

$^1$H-NMR (CDCl$_3$) δ 7.52-7.64 (m, 3H), 7.45 (t, J=7.6 Hz, 2H), 7.38 (d, J=8.3 Hz, 2H), 7.06 (d, J=8.3 Hz, 2H), 6.70 (s, 1H), 6.09 (t, J=2.6 Hz, 1H), 5.85 (s, 1H), 5.65 (t, J=1.6 Hz, 1H), 4.03-4.21 (m, 3H), 3.60-3.71 (m, 2H), 3.35 (s, 3H), 3.19 (s, 3H). Mass Spectrum (ESI) m/e=423.1 (M+23).

Example 8

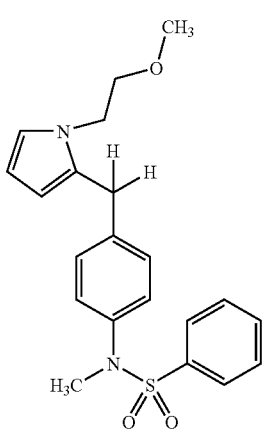

N-(4-{1-[1-(2-methoxyethyl)-1H-pyrrol-2-yl]-methyl}-phenyl)-N-methyl-benzenesulfonamide To a solution of 16 mg (0.04 mmol) of N-(4-{1-hydroxy-1-[1-(2-methoxyethyl)-1H-pyrrol-2-yl]-methyl}-phenyl)-N-methyl-benzenesulfonamide (Example 7) in 1.5 mL CH$_2$Cl$_2$ at 0° C. were added 620 μL (3.88 mmol) of triethylsilane followed by 100 μL (0.79 mmol) of boron trifluoride diethyl etherate dropwise. The mixture was warmed to room temperature and stirred for 2.5 h. After this time, the reaction mixture was cooled to 0° C., quenched by the addition of a saturated aqueous solution of sodium bicarbonate, allowed to warm to room temperature, and extracted with EtOAc. The combined organic layers were dried over Na$_2$SO$_4$, filtered and the filtrate was concentrated. The residue was purified by chromatography on silica gel (hexanes:EtOAc, 3:1) to give the title compound.

$^1$H-NMR (CDCl$_3$) δ 7.52-7.60 (m, 3H), 7.45 (t, J=7.7 Hz, 2H), 7.09 (d, J=8.4 Hz, 2H), 7.00 (d, J=8.4 Hz, 2H), 6.68 (t, J=2.0 Hz, 1H), 6.10 (t, J=3.1 Hz, 1H), 5.85 (s, 1H), 3.95 (s, 2H), 3.88 (t, J=5.8 Hz, 2H), 3.45 (t, J=5.8 Hz, 2H), 3.27 (s, 3H), 3.16 (s, 3H). Mass Spectrum (ESI) m/e=407.1 (M+23).

Preparative Example A

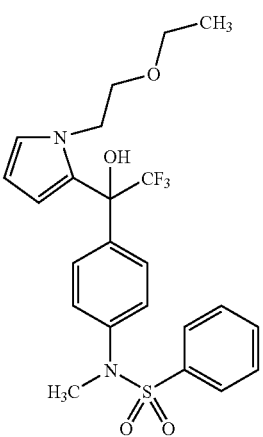

N-(4-{1-[1-(2-Ethoxyethyl)-1H-pyrrol-2-yl]-2,2,2-trifluoro-1-hydroxyethyl}-phenyl)-N-methyl-benzenesulfonamide

Step A. N-Ethoxyethyl-2-trifluoroacetylpyrrole

To a suspension of 268 mg (6.70 mmol) of NaH (60% dispersion in oil) in 20 mL DMF at 0° C. was added 1.01 g (6.19 mmol) of 2-(trifluoroacteyl)pyrrole and the mixture was stirred at 0° C. for 1 h. After this time, 765 μL (6.51 mmol) of 2-bromoethyl ethyl ether was added and the mixture was warmed to 60° C. and stirred for 16 h. After this time, the reaction mixture was allowed to cool to room temperature, quenched by the addition of a saturated aqueous solution of ammonium chloride, and extracted with EtOAc. The organic layer was washed with water and brine, dried over Na$_2$SO$_4$, filtered and the filtrate was concentrated. The residue was purified by chromatography on silica gel (pure hexanes grading to hexanes:EtOAc, 97:3) to give the title compound.

$^1$H-NMR (CDCl$_3$) δ 7.19 (s, 1H), 6.25-6.30 (m, 1H), 4.52 (t, J=5.1 Hz, 1H), 3.69 (t, J=5.4 Hz, 2H), 3.42 (q, J=7.0 Hz, 2H), 1.13 (t, J=7.0 Hz, 3H). Mass Spectrum (ESI) m/e=190 (M−45).

Step B. 4-Bromo-N-methylaniline

The title compound was prepared via N-methylation of 4-bromoaniline following standard methods (see, also Example 1, Step A of U.S. application Ser. No. 10/354,922, now U.S. Pat. No. 7,071,358) $^1$H-NMR (DMSO) δ 2.64 (s, 3H), 5.82 (brs, 1H), 6.46-6.49 (m, 2H), 7.18-7.21 (m, 2H).

Step C. N-(4-Bromophenyl)-N-methyl-benzenesulfonamide

A solution of 0.61 g (3.3 mmol) of 4-bromo-N-methylaniline and 0.5 mL (3.92 mmol) of benzenesulfonyl chloride in 5 mL of pyridine was stirred for 12 h at rt. After that time the pyridine was removed by azeotropic distillation with heptane.

The residue was purified by chromatography on silica (hexanes:EtOAc, 9:1) to give the title compound.

$^1$H NMR (DMSO) δ 3.12 (s, 3 H), 7.04-7.08 (m, 2 H), 7.50-7.62 (m, 6 H), 7.69-7.74 (m, 1 H).

Step D. N-(4-{1-[1-(2-Ethoxyethyl)-1H-pyrrol-2-yl]-2,2,2-trifluoro-1-hydroxyethyl}-phenyl)-N-methyl-benzenesulfonamide To a solution of 75 mg (0.23 mmol) of N-(4-bromophenyl)-N-methyl-benzenesulfonamide in 4 mL of Et$_2$O at −78° C. was added dropwise 285 μL (0.49 mmol) of a 1.7 M solution of tert-BuLi in pentane and the resultant mixture was stirred at −78° C. for 10 min. To this mixture was then added a solution of 81 mg (0.34 mmol) of N-ethoxyethyl-2-trifluoroacetylpyrrole in 3 mL THF and the mixture was allowed to gradually warm to room temperature over an 18 h period. The reaction mixture was quenched by the addition of a saturated aqueous solution of ammonium chloride and extracted with EtOAc. The combined organic layers were dried over Na$_2$SO$_4$, filtered and the filtrate was concentrated. The residue was purified by chromatography on silica gel (hexanes:EtOAc, 4:1) to give the title compound.

$^1$H-NMR (CDCl$_3$) δ 7.49-7.60 (m, 3H), 7.42 (t, J=7.4 Hz, 2H), 7.32 (d, J=8.5 Hz, 2H), 7.06 (d, J=8.7 Hz, 2H), 6.67 (dd, J=2.7 Hz, 1.7 Hz, 1H), 6.45-6.50 (m, 1H), 6.20 (t, J=3.3 Hz, 1H), 5.82 (s, 1H), 3.76-3.85 (m, 1H), 3.55-3.65 (m, 2H), 3.43-3.52 (m, 2H), 3.29-3.38 (m, 1H), 3.17 (s, 3H), 1.15 (t, J=7.0 Hz, 3H). Mass Spectrum (ESI) m/e=505.1 (M+23).

Preparative Example B

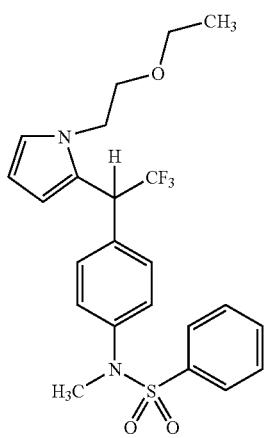

N-(4-{1-[1-(2-Ethoxyethyl)-1H-pyrrol-2-yl]-2,2,2-trifluoroethyl}-phenyl)-N-methyl-benzenesulfonamide To a solution of 32 mg (0.07 mmol) of N-(4-{1-[1-(2-ethoxyethyl)-1H-pyrrol-2-yl]-2,2,2-trifluoro-1-hydroxyethyl}-phenyl)-N-methyl-benzenesulfonamide (see, Preparative Example A) in 2 mL of CH$_2$Cl$_2$ at 0° C. were added 1.05 mL (6.57 mmol) of triethylsilane followed by 167 μL (1.32 mmol) of boron trifluoride diethyl etherate dropwise. The mixture was warmed to room temperature and stirred for 1.75 h. After this time, the reaction mixture was cooled to 0° C., quenched by the addition of a saturated aqueous solution of sodium bicarbonate, allowed to warm to room temperature, and extracted with EtOAc. The combined organic layers were dried over Na$_2$SO$_4$, filtered and the filtrate was concentrated. The residue was purified by chromatography on silica gel (hexanes:EtOAc, 4:1) to give the title compound.

$^1$H-NMR (CDCl$_3$) δ 7.50-7.61 (m, 3H), 7.41-7.49 (m, 2H), 7.22-7.28 (m, 2H), 7.07 (d, J=8.3 Hz, 2H), 6.66 (s, 1H), 6.32 (s, 1H), 6.18 (t, J=3.2 Hz, 1H), 5.06 (q, J$_{C-F}$=9.2 Hz, 1H), 3.79-3.83 (m, 2H), 3.31-3.57 (m, 4H), 3.14 (s, 3H), 1.13 (t, J=7.0 Hz, 3H). Mass Spectrum (ESI) m/e=489.1 (M+23).

What is claimed is:

1. A method of modulating LXR function in a cell, said method comprising contacting said cell with an LXR-modulating amount of a compound of the formula:

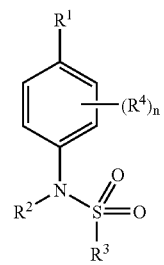

wherein
R$^1$ is

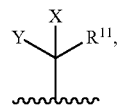

wherein
R$^{11}$ is pyrrolyl, optionally substituted with from one to four substituents independently selected from the group consisting of halogen, cyano, nitro, R$^{14}$, OR$^{13}$, SR$^{13}$, N(R$^{13}$)$_2$, NHSO$_2$R$^{14}$, NHC(O)R$^{13}$, phenyl, phenyl(C$_1$-C$_8$)alkyl, and phenyl(C$_2$-C$_8$)heteroalkyl; wherein each R$^{13}$ is independently selected from H, (C$_1$-C$_8$)alkyl, (C$_3$-C$_8$)alkenyl, (C$_3$-C$_8$)alkynyl, (C$_2$-C$_8$)heteroalkyl and halo(C$_1$-C$_8$)alkyl and each R$^{14}$ is independently selected from (C$_1$-C$_8$)alkyl, (C$_3$-C$_8$)alkenyl, (C$_3$-C$_8$)alkynyl, (C$_2$-C$_8$)heteroalkyl and halo(C$_1$-C$_8$)alkyl;

X is a member selected from the group consisting of OH and OR$^{15}$, wherein R$^{15}$ is (C$_1$-C$_8$)alkyl, (C$_3$-C$_8$)alkenyl, (C$_3$-C$_8$)alkynyl, (C$_2$-C$_8$)heteroalkyl or halo(C$_1$-C$_8$)alkyl;

Y is H, (C$_1$-C$_8$)alkyl, (C$_3$-C$_8$)cycloalkyl, (C$_3$-C$_8$)alkenyl, (C$_3$-C$_8$)alkynyl or (C$_2$-C$_8$)heteroalkyl; with the proviso that when Y is a substituted (C$_1$-C$_8$)alkyl, the substituents are other than fluorine atoms;

R$^2$ is a member selected from the group consisting of H, (C$_1$-C$_8$)alkyl, (C$_2$-C$_8$)heteroalkyl, (C$_3$-C$_8$)alkenyl, (C$_3$-C$_8$)alkynyl, (C$_3$-C$_8$)cycloalkyl and (C$_4$-C$_8$)cycloalkyl-alkyl, wherein any alkyl portions of R$^2$ are optionally substituted with from one to three substituents independently selected from halogen, nitro, cyano, hydroxy, oxo and amino;

R$^3$ is aryl optionally substituted with from one to five substituents independently selected from the group consisting of halogen, cyano, nitro, R$^{16}$, OR$^{16}$, SR$^{16}$, COR$^{16}$, CO$_2$R$^{16}$, NHR$^{16}$, N(R$^{16}$)$_2$, CONHR$^{16}$, CON $(R^{16})_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl;

the subscript n is an integer of from 0 to 3; and each $R^4$ is independently selected from the group consisting of halogen, cyano, nitro, $R^{17}$, $OR^{17}$, $SR^{17}$, $COR^{17}$, $CO_2R^{17}$, $N(R^{17})_2$ and $CON(R^{17})_2$, wherein each $R^{17}$ is independently selected from H, ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl;

or a pharmaceutically acceptable salt thereof.

2. A method of treating obesity, diabetes, hypercholesterolemia, atherosclerosis or hypolipoproteinemia, comprising administering to a subject in need thereof, a therapeutically effective amount of a compound of formula:

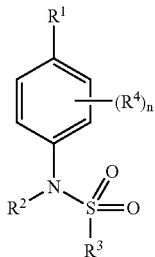

wherein
R is

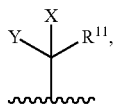

wherein
$R^{11}$ is pyrrolyl, optionally substituted with from one to four substituents independently selected from the group consisting of halogen, cyano, nitro, $R^{14}$, $OR^{13}$, $SR^{13}$, $N(R^{13})_2$, $NHSO_2R^{14}$, $NHC(O)R^{13}$, phenyl, phenyl($C_1$-$C_8$)alkyl, and phenyl($C_2$-$C_8$)heteroalkyl; wherein each $R^{13}$ is independently selected from H, ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl and each $R^{14}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl;

X is a member selected from the group consisting of OH and $OR^{15}$, wherein $R^{15}$ is ($C_1$-$C_8$)alkyl, ($C_3$-$C_8$)alkenyl, ($C_3$-$C_8$)alkynyl, ($C_2$-$C_8$)heteroalkyl or halo($C_1$-$C_8$)alkyl;

Y is H, ($C_1$-$C_8$)alkyl, ($C_3$-$C_8$)cycloalkyl, ($C_3$-$C_8$)alkenyl, ($C_3$-$C_8$)alkynyl or ($C_2$-$C_8$)heteroalkyl; with the proviso that when Y is a substituted ($C_1$-$C_8$)alkyl, the substituents are other than fluorine atoms;

$R^2$ is a member selected from the group consisting of H, ($C_1$-$C_8$)alkyl, ($C_2$-$C_8$)heteroalkyl, ($C_3$-$C_8$)alkenyl, ($C_3$-$C_8$)alkynyl, ($C_3$-$C_8$)cycloalkyl and ($C_4$-$C_8$)cycloalkylalkyl, wherein any alkyl portions of $R^2$ are optionally substituted with from one to three substituents independently selected from halogen, nitro, cyano, hydroxy, oxo and amino;

$R^3$ is aryl optionally substituted with from one to five substituents independently selected from the group consisting of halogen, cyano, nitro, $R^{16}$, $OR^{16}$, $SR^{16}$, $COR^{16}$, $CO_2R^{16}$, $NHR^{16}$, $N(R^{16})_2$, $CONHR^{16}$, $CON(R^{16})_2$, $NHSO_2R^{16}$, $NHC(O)R^{16}$, phenyl, phenyl($C_1$-$C_8$)alkyl, and phenyl($C_2$-$C_8$)heteroalkyl; wherein each $R^{16}$ is independently selected from ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl;

the subscript n is an integer of from 0 to 3; and each $R^4$ is independently selected from the group consisting of halogen, cyano, nitro, $R^{17}$, $OR^{17}$, $SR^{17}$, $COR^{17}$, $CO_2R^{17}$, $N(R^{17})_2$ and $CON(R^{17})_2$, wherein each $R^{17}$ is independently selected from H, ($C_1$-$C_8$)alkyl, ($C_3$-$C_8$)alkenyl, ($C_3$-$C_8$)alkynyl, ($C_2$-$C_8$)heteroalkyl and halo($C_1$-$C_8$)alkyl;

or a pharmaceutically acceptable salt thereof.

3. A method in accordance with claim 2, wherein said compound is administered in combination with an anti-hypercholesterolemic agent.

4. A method in accordance with claim 2, wherein said compound is an LXR agonist.

5. A method in accordance with claim 2, wherein said condition is obesity.

6. A method in accordance with claim 2, wherein said condition is diabetes.

7. A method in accordance with claim 2, wherein said condition is hypercholesterolemia.

8. A method in accordance with claim 2, wherein said condition is atherosclerosis.

9. A method in accordance with claim 2, wherein said condition is hyperlipoproteinemia.

* * * * *